United States Patent [19]

Buysch et al.

[11] 4,430,452

[45] Feb. 7, 1984

[54] STABILIZER-CONTAINING REACTIVE COMPONENTS FOR PU-FOAMS, NEW STABILIZERS AND A PROCESS FOR PRODUCING THESE STABILIZERS

[75] Inventors: Hans-Josef Buysch, Krefeld; Hans-Walter Illger, Roesrath; Karl H. Dorner, Pulheim, all of Fed. Rep. of Germany

[73] Assignee: Bayer Aktiengesellschaft, Leverkusen, Fed. Rep. of Germany

[21] Appl. No.: 395,552

[22] Filed: Jul. 6, 1982

[30] Foreign Application Priority Data

Jul. 14, 1981 [DE] Fed. Rep. of Germany ....... 3127750

[51] Int. Cl.³ .............................................. C08J 9/36
[52] U.S. Cl. ..................................... 521/107; 521/121; 544/32; 544/35; 544/57; 544/102
[58] Field of Search ................. 521/121, 107; 544/32, 544/35, 57, 102, 344

[56] References Cited

U.S. PATENT DOCUMENTS

| | | | |
|---|---|---|---|
| 3,146,272 | 8/1964 | Lloyd | 544/35 X |
| 3,214,397 | 10/1965 | Cox | 260/2.5 |
| 3,437,694 | 4/1969 | Austin | 260/611.5 |
| 3,489,749 | 1/1970 | Randell | 544/35 |
| 3,494,880 | 2/1970 | Austin | 260/2.5 |
| 3,539,515 | 11/1970 | McCabe | 544/35 X |
| 3,567,664 | 3/1971 | Haring | 260/2.5 |
| 3,637,865 | 1/1972 | Haring | 260/611.5 |
| 3,689,484 | 9/1972 | Spilners | 544/35 |
| 3,798,184 | 3/1974 | Cuscureda et al | 260/2.5 BB |
| 3,803,140 | 4/1974 | Cook et al. | 544/35 |
| 4,007,230 | 2/1977 | Hinze | 260/611.5 |
| 4,010,211 | 3/1977 | Preston | 260/611.5 |
| 4,143,219 | 3/1979 | Hensch | 521/107 |
| 4,146,687 | 3/1979 | Reale | 521/107 |
| 4,235,975 | 11/1980 | Preston | 521/107 |
| 4,275,173 | 6/1981 | Henze | 260/611.5 |
| 4,264,767 | 4/1981 | Quinlan | 544/57 |
| 4,374,966 | 2/1983 | Fischer | 544/102 X |

OTHER PUBLICATIONS

Chem. Abstracts, Band 77, Nr. 23, Dec. 4, 1972, pg. 71, No. 153541s Japenese 72, 19,088 Kawaguchi Chemical Industry Co., Ltd., Jun. 1, 1972.

*Primary Examiner*—Lucille M. Phynes
*Attorney, Agent, or Firm*—Gene Harsh; Joseph C. Gil

[57] ABSTRACT

The invention relates to stabilizer-containing reactive components for the production of polyurethane foams having little or no tendency towards core discoloration which are characterized by a stabilizing addition of monomeric and/or oligomeric derivatives of the diphenylamine series, including the phenothiazine series. The invention also relates to new stabilizers of the diphenylamine and/or phenothiazine series and to a process for their production, characterized in that aromatic amines of the diphenylamine and/or phenothiazine series are reacted with bifunctional halogen derivatives, diols, bis-ethers or bis-esters or with bis-olefins formed therefrom at elevated temperatures in the presence of strong acids and the amines are optionally further alkylated.

6 Claims, No Drawings

STABILIZER-CONTAINING REACTIVE COMPONENTS FOR PU-FOAMS, NEW STABILIZERS AND A PROCESS FOR PRODUCING THESE STABILIZERS

This invention relates to stabilizer-containing reactive components for the production of polyurethane foams which have little or no tendency towards core discoloration and which are characterized by a stabilizing addition of monomeric and/or oligomeric derivatives of the diphenylamine series, including the phenothiazine series. This invention also relates to new stabilizers of te diphenylamine and/or phenothiazine series and to a process for their production.

Polyurethane foams having a variety of physical properties have long been produced on a large scale by the isocyanate polyaddition process from compounds containing several active H-atoms, particularly compounds containing OH— and COOH— groups, and polyisocyanates, optionally in conjunction with water and/or other blowing agents, activators, emulsifiers, foam stabilizers and oxidation inhibitors (see, e.g., Vieweg/Hochtlen, Kunststoff-Handbuch, Vol. VII, Polyurethane, Carl-Hanser-Verlag, Munich 1966). It is possible in this way to produce both flexible and rigid foams and intermediate variants, depending upon the type of components used.

Polyurethane foams are preferably produced by mixing components in liquid form. The starting materials to be reacted with one another are either mixed in their original form to create the foam, or a preadduct containing NCO— groups is produced from polyhydroxyl compounds (such as polyalkylene glycol ethers or polyesters containing OH— groups) and an excess of polyisocyanate and then subsequently converted into the foam in a second step.

During the foaming reaction—particularly when the foams being produced have low densities or when a relatively large quantity of isocyanate or water is used—undesirable brownish to dark brown discoloration occurs in the foam block. This discoloration occurs primarily in the core of the block where the temperature prevailing during the foaming reaction is at its highest and takes the longest to cool and is generally accompanied by damage to the foam (reflected in a considerable reduction in the level of its mechanical properties). Although the discoloration and accompanying damage may lead to foams which cannot be used with obvious economic disadvantages, a much greater concern when foaming on an industrial scale lies in the possible spontaneous ignition of large foam masses. Products having a tendency towards core discoloration can spontaneously ignite, possibly leading to major fires with serious consequences. This risk can be increased even more by additives of the type used during the foaming process, such as, for example, tertiary amines which are used as catalysts, halogenated hydrocarbons used as blowing agents and halogen-containing phosphoric acid esters used as flameproofing agents.

Accordingly, numerous proposals have been put forward with a view to suppressing core discoloration and core scorching.

Certain, but still inadequate, advances have been made by the addition of sterically hindered phenols (cf. U.S. Pat. Nos. 3,494,880 and 3,437,694). The same applies to the use of phenothiazine (cf. U.S. Pat. Nos. 3,214,397 and 4,143,219). An improvement was also obtained by using a combination of dioctyl diphenylamine and 2,6-di-tert.-butyl-p-cresol (ionol) (cf. U.S. Pat. Nos. 3,567,664 and 3,637,865). Finally, the ionol may be partly replaced by phenothiazine, generally without any change in the stabilizing effect which, in some cases, is even slightly improved (U.S. Pat. No. 4,010,211).

Accordingly, the object of the present invention is to provide stabilized reactive components for the production of polyurethane foams characterized by considerably improved stabilization against core discoloration, particularly core scorching, and against spontaneous ignition during the foam-forming reaction.

It has now been found that stabilized polyurethane foams can be obtained by using compounds of the diphenylamine series, including the phenothiazine series, as stabilizers in the reactive components during the foam-forming reaction.

DESCRIPTION OF THE INVENTION

Accordingly, the present invention relates to stabilizer-containing reactive components for the production of polyurethane foams having little or no tendency towards core discoloration which are based on polyisocyanates, polyols and, optionally, water, blowing agents, catalysts, other stabilizers and standard additives, characterized in that they contain, as stabilizers, monomeric and/or oligomeric derivatives of the diphenylamine series of compounds (including the phenothiazine series), in stabilizing quantities of from 0.02 to 5%, by weight, which stabilizers correspond to the general formulae I to V:

(a) general formula (I):

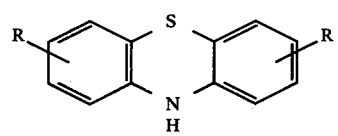

wherein R represents $C_7$–$C_{18}$-aralkyl (preferably $C_7$–$C_{12}$-aralkyl) (the number of carbonatoms indicates the total number in the aryl radical, including its alkyl substituents);

(b) general formula II;

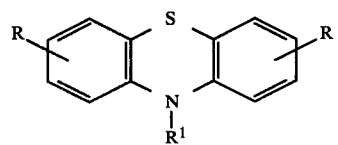

wherein
R is as defined above;
$R^1$ represents $C_1$–$C_{18}$-alkyl (preferably a $C_1$–$C_6$-alkyl), a $C_5$–$C_{12}$-cycloalkyl or cycloalkenyl (preferably a $C_5$–$C_6$-cycloalkyl); a $C_7$–$C_{18}$-aralkyl (preferably a $C_7$–$C_{12}$-aralkyl) which may optionally be substituted by OH, SH, ether, thioether, carbonic ester, carbonamide and carboxyl groups or which may be interrupted by such groups (other than OH, SH, COOH— groups) and olefinic double bonds, a radical —C—A—$R^2$; or a radical corresponding to the following formula

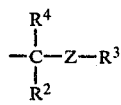

wherein
R², R³ and R⁴ may be the same or different and represent H, a C₁–C₁₂-alkyl, a C₅–C₁₂-cycloalkyl or cycloalkenyl (preferably a C₅- and C₆-cycloalkyl); a C₇–C₁₂-aralkyl (preferably a C₇–C₁₀-aralkyl); in addition to which R₂ represents optionally substituted aryl and, together with R⁴ and the central C-atom, may form a 5- to 12-member (preferably 5- or 6-member) aliphatic ring; and Z represents O, S, NH, NR⁵, where R⁵=R² or a radical of the formula CO—A—R², wherein A is a single bond, S, O, NH or NR² (here and in the following, R² does not form a ring with R⁴), or Z together with R³ also represents the radical

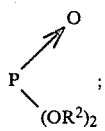

and
(c) general formula III):

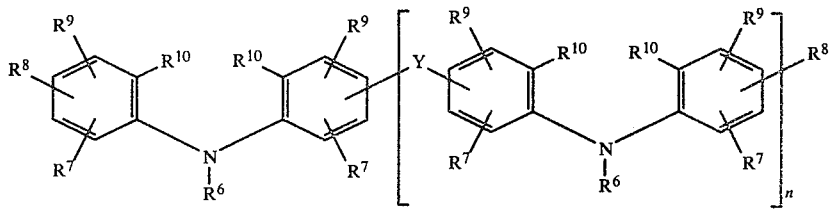

wherein
R⁶ represents hydrogen or R¹ (as defined above),
R⁷, R⁹ and R¹⁰ may be the same or different and represent H, CH₃ or C₂H₅ (preferably H);
R⁸ represents H, benzyl, styryl, α-methyl-styryl, tert.-butyl, tert.-amyl,

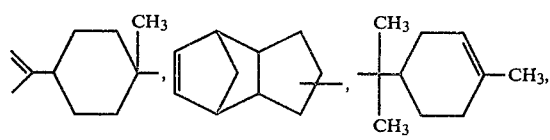

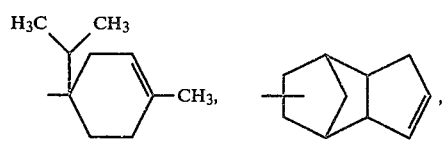

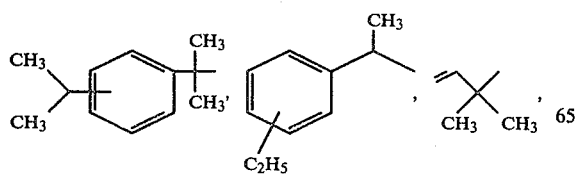

or, less preferably,

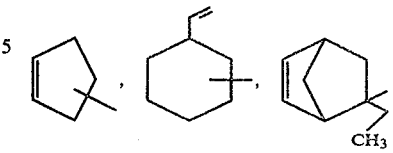

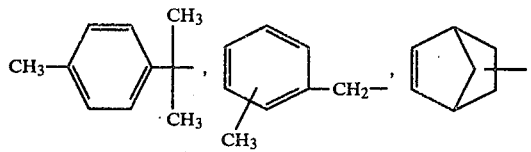

isonyl, cyclohexyl or methylcyclohexyl,
Y represents

where R⁷ is as defined above, but preferably represents H whilst R¹¹ represents a C₁–C₇-alkyl (preferably a C₁–C₄-alkyl), or a cyclohexyl, a cyclohexenyl an aryl; or

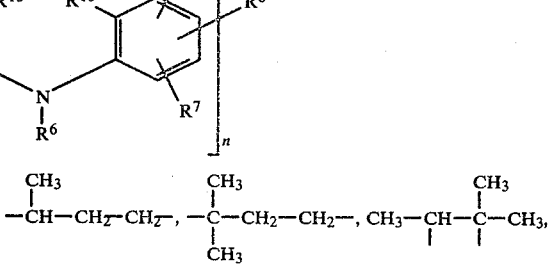

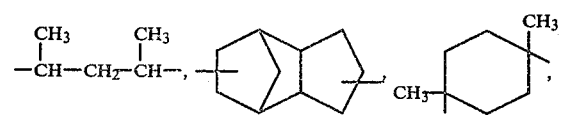

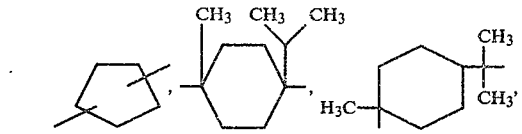

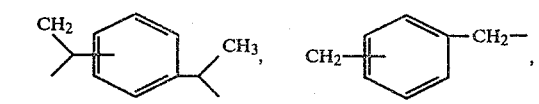

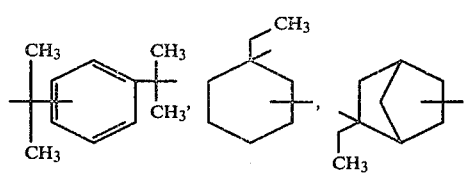

and, up to 60 mole percent, also —S—, —CH$_2$—, —CH$_2$—S—CH$_2$— or —CH$_2$O—CH$_2$— (preferably —CH$_2$—) and n is an integer of from 1 to 29 and preferably from 1 to 19;

general formula IV

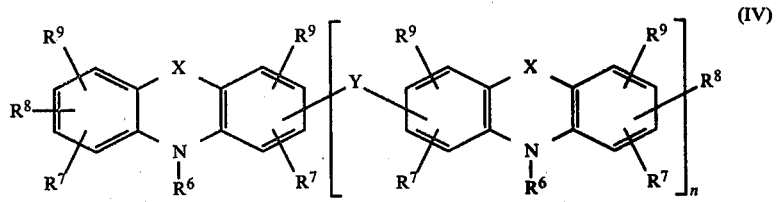

wherein

X represents a single bond, CH$_2$, CH, S, O, NR$^5$, CR$^7$R$^{11}$ or POH, preferably CH$_2$, S, NR$^5$ and, more preferably, S; and general formula V

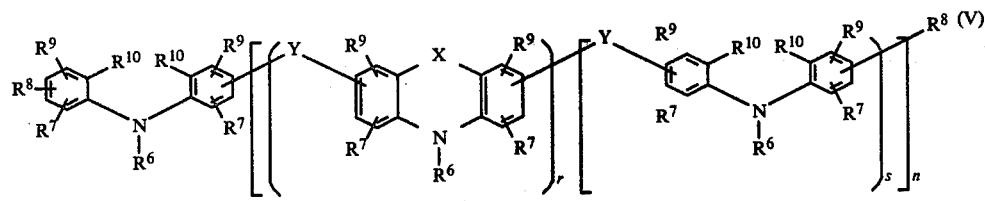

wherein r and s are integers of from 1 to 29 and preferably from 1 to 9, and

R$_1$–R$_{10}$, and Y as defined above.

Reactive polyurethane compositions protected with these compounds may also be processed with correspondingly high percentages of isocyanate or water to form foams of very low density, in which case core scorching and spontaneous ignition may be safely ruled out. Comparable formulations containing conventional stabilisers undergo at least deep brown core discolouration, in many cases core scorching or even burning of the block.

The substances to be added to the starting materials or mixtures of starting materials in accordance with the invention are used in stabilising quantities, for example in quantities of from 0.02 to 5.0% by weight, preferably in quantities of from 0.05 to 2.5% by weight and, more preferably, in quantities of from 0.07 to 1.5% by weight, based on the polyurethane mass as a whole. They may be added in the form of a concentrate in an inert solvent or in solution in the additives required for polyurethane production, such as catalysts or flameproofing agents, or in the actual reactants, namely the polyol or polyisocyanate components.

The monomeric and, in particular, the oligomeric mixtures of stabilisers corresponding to general formulae III to V are preferred, although compounds corresponding to general formulae IV and V are particularly preferred. The best results are obtained with stabilisers corresponding to formula IV.

These stabilisers may also be used in combination with other known stabilisers from the sterically hindered phenol series, from the phosphorous acid ester series, from the phosphine series and from the thioether series, in which case synergistic increases in effectiveness may actually be observed.

The following are examples of suitable substances for mixed stabilisers: phenols corresponding to the following formula

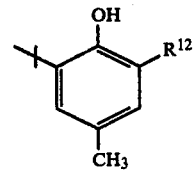

in which R$^{12}$ represents methyl, tert.-butyl, tert.-amyl, cyclohexyl, cyclopentyl; phosphines and phosphites corresponding to the following formulae

P(SR$^{13}$)$_3$, P(OR$^{13}$)$_3$, and thioethers corresponding to the following formulae S(R$^{13}$)$_2$ and S(CH$_2$CH$_2$COOR$^{13}$)$_2$ in which R$^{13}$ represents a C$_2$–C$_{20}$-alkyl, C$_5$–C$_{12}$-cycloalkyl or C$_6$–C$_{10}$-aryl radical, specific examples of these substances being 2,6-di-tert.-butyl-p-cresol, 2-tert.-butyl-6-cyclohexyl-p-cresol, triphenyl phosphine, tris-(p-N,N-dimethylphenyl)-phosphine, di-(nonylphenyl)-phosphite, tri-(nonylphenyl)-phosphite, tri-(2,4-di-tert.-butylphenyl)-phosphite, triphenyl phosphite, tributyl phosphite, tris-dipropylene glycol phosphite and dilauryl thiodipropionate.

The present invention also relates to new compounds corresponding to general formula III:

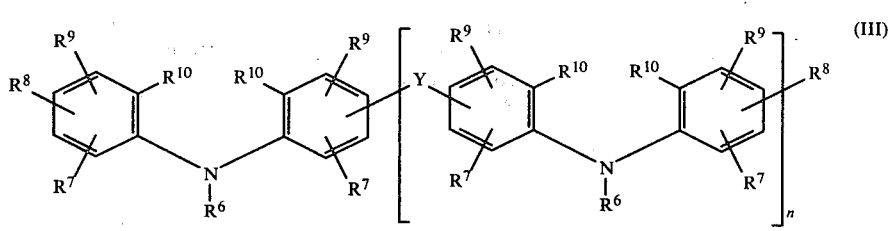

wherein
R⁶ represents hydrogen or R¹ which represents a C₁–C₁₈-alkyl (preferably C₁–C₆-alkyl); C₅–C₁₂-cycloalkyl or cycloalkenyl (preferably a C₅–C₆-cycloalkyl); a C₇–C₁₈-aralkyl (preferably a C₇–C₁₂-aralkyl) which may optionally be substituted by OH, SH, ether, thioether, carbonic ester, carbon-amide and carboxyl groups or which may be interrupted by such groups (other than OH, SH, COOH— group) and olefinic double bonds; a radical

or a radical of the formula

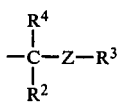

where R², R³, and R⁴ are the same or different and represent H; a C₁–C₁₂-alkyl; a C₅–C₁₂-cycloalkyl or cycloalkenyl (preferably a C₅–C₆-cycloalkyl); a C₇–C₁₂-aralkyl (preferably a C₇–C₁₀-aralkyl); in addition to which R₂ represents optionally substituted aryl and, together with R⁴ and the central C-atom, forms a 5- to 12-member (preferably 5- or 6 member) aliphatic ring; and Z represents O, S, NH, NR⁵, where R⁵=R² or a radical of the formula CO—A—R², wherein A is a single bond, S, O, NH or NR² (here and in the following, R² does not form a ring with R⁴), Z together with R³ represents the radical $$\begin{array}{c} \quad\quad O \\ \quad\nearrow\!\!\!\!\nearrow \\ P \\ \quad\searrow \\ \quad(OR^2)_2 \end{array}$$

R⁷, R⁹ and R¹⁰ may be the same or different and represent H, CH₃ or C₂H₅ (preferably H);
R⁸ represents H, benzyl, styryl, α-methylstyryl, tert.-butyl, tert.-amyl,

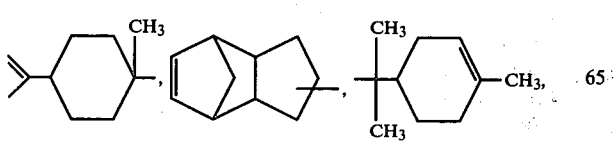

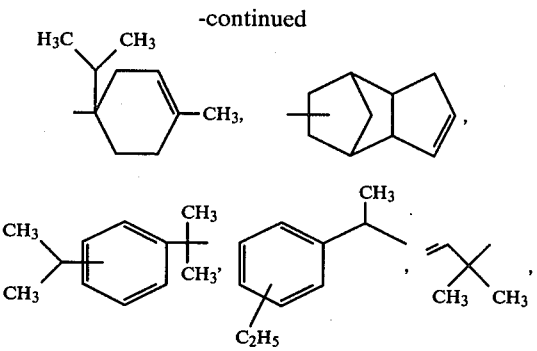

or less preferably,

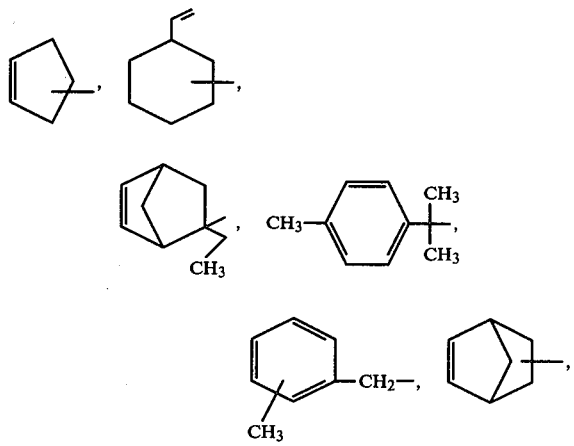

isononyl, cyclohexyl or methyl cyclohexyl;
Y represents

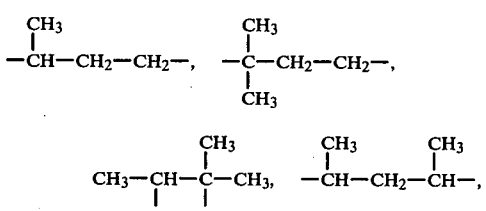

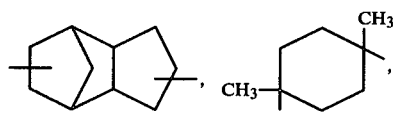

-continued

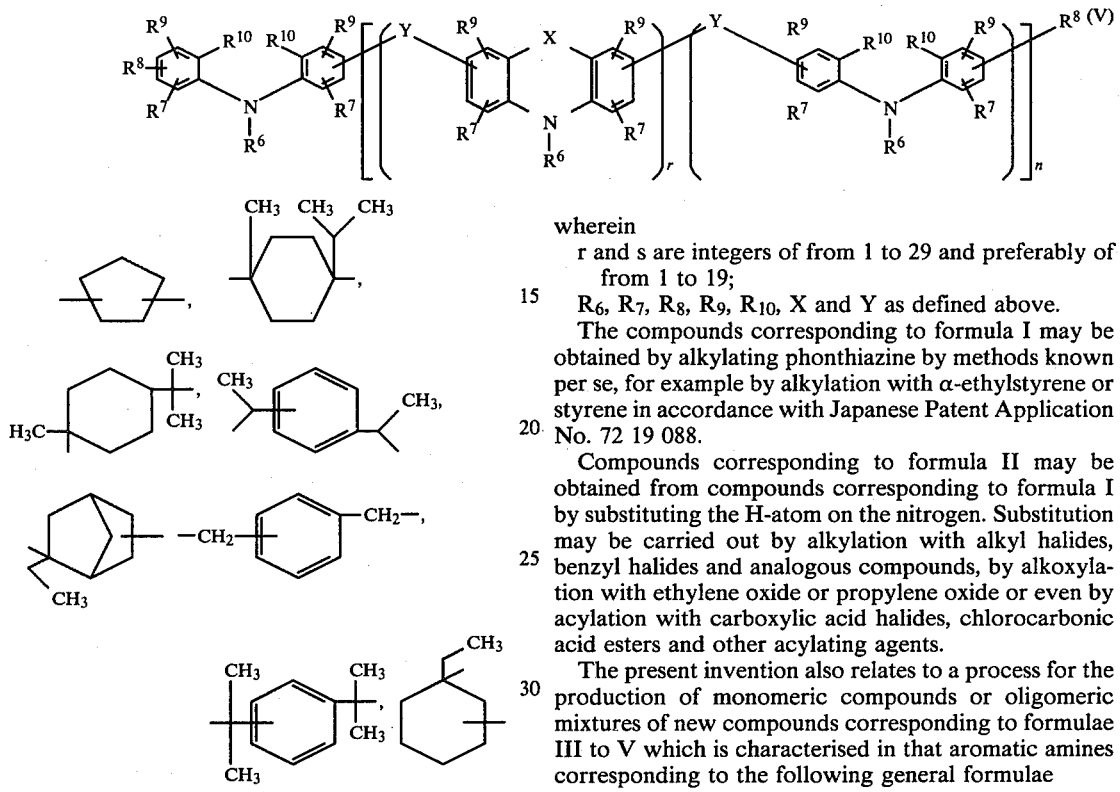

or up to 60 mole percent, also —S—, —CH$_2$—, —CH$_2$—S—CH$_2$— or —CH$_2$O—CH$_2$ (preferably —CH$_2$—); and n is an integer of from 1 to 29 and preferably from 1 to 19.

Additionally, the present invention relates to new compounds corresponding to the general formula IV:

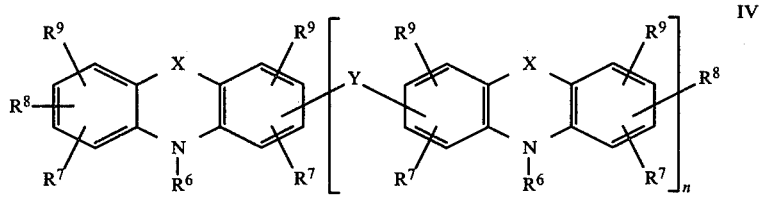

wherein
Y represents

where R$^7$ is as defined above, but preferably represents H, whereas R$^{11}$ represents a C$_1$-C$_7$- (preferably a C$_1$-C$_4$-) alkyl, cyclohexyl, cyclohexenyl and aryl; and Y may also have the further meanings defined in general formula III;

X represents a single bond, CH$_2$, CH, S, O, NR$^5$, CR$^7$R$^{11}$ or POH, preferably CH$_2$, S, NR$^5$ and more preferably, S.

Finally the present invention relates to new compounds relating to general formula V, wherein
r and s are integers of from 1 to 29 and preferably of from 1 to 19;
R$_6$, R$_7$, R$_8$, R$_9$, R$_{10}$, X and Y as defined above.

The compounds corresponding to formula I may be obtained by alkylating phonthiazine by methods known per se, for example by alkylation with α-ethylstyrene or styrene in accordance with Japanese Patent Application No. 72 19 088.

Compounds corresponding to formula II may be obtained from compounds corresponding to formula I by substituting the H-atom on the nitrogen. Substitution may be carried out by alkylation with alkyl halides, benzyl halides and analogous compounds, by alkoxylation with ethylene oxide or propylene oxide or even by acylation with carboxylic acid halides, chlorocarbonic acid esters and other acylating agents.

The present invention also relates to a process for the production of monomeric compounds or oligomeric mixtures of new compounds corresponding to formulae III to V which is characterised in that aromatic amines corresponding to the following general formulae (wherein the radicals R$_6$, R$_7$, R$_8$, R$_9$, R$_{10}$ and X are as defined above) are reacted with bifunctional compounds corresponding to the following formulae Hal—Y—Hal (Hal = halogen)

HO—Y—OH

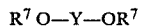

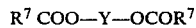

or with bis-olefins formed from these compounds by elimination of the radical HOH, HOR$^7$, HOCOR$^7$ or H Hal, at temperatures of from 50° to 300° C. and preferably, from 120° to 250° C., in the presence of strong acids having a pk$_s$-value of less than 2. The radicals R$^8$ and R$^6$ (as defined above, except that neither represents hydrogen) may be introduced before, during or after the above reaction of the amines.

The new stabilisers according to the invention corresponding to formulae III to V may also be obtained by reacting the aromatic amines diphenylamine, phenothiazine, phenoxazine, phenazine, phenphosphazine, acridine, carbazol or the amines correspondingly substituted by R$^6$, R$^7$ and R$^9$ either in pure form or in admixture with the bifunctional compounds on which the linking unit Y (cf. the general formula of the new compounds) is based, i.e. with the corresponding hydroxy compounds, ethers, halides, olefins and esters.

By way of example, the following compounds may be used to introduce the linking —Y-unit (VI)

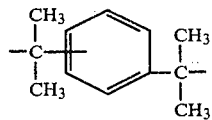

(VI)

for producing compounds (III) to (V):

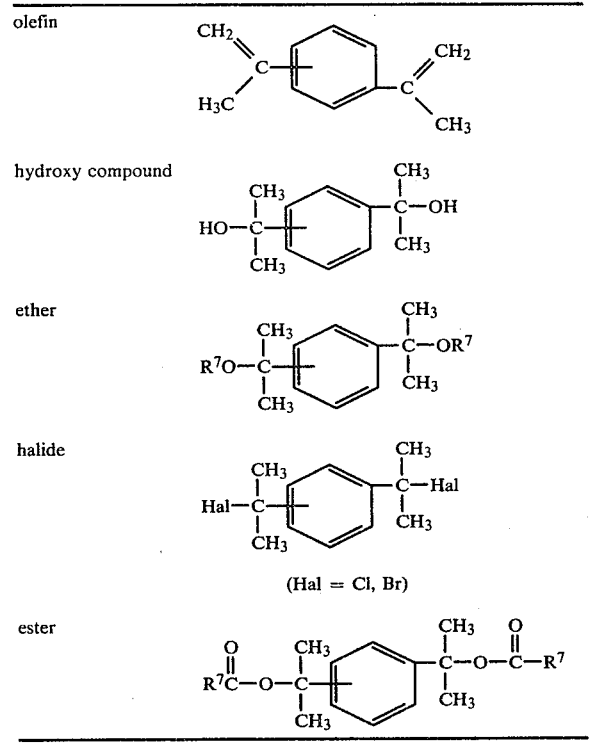

(wherein R$^7$ is as defined above).

The compounds either have a direct alkylating effect on the aromatic amine compound (like the above olefin) or an indirect alkylating effect (following elimination of the radical H$_2$O, R$^7$.OH, HCl or HBr or R$^7$COOH) and result in the linkage of two aromatic amines in the ortho position or in the para position to the nitrogen atom.

The radical R$^8$ (where R$^8$ does not represent H) is introduced during the above-described reaction (again in the ortho position or in the para position) by using an excess of the alkylating compound on which Y is based. It may also be subsequently introduced by alkylating compounds corresponding to formulae III to V, which also contain hydrogen in the R$^8$ position, with a corresponding alkylating compound, such as styrene, α-ethylstyrene, benzyl alcohol, cyclohexene, isononylene, isobutylene under the synthesis conditions decribed above. Alternatively, a compound already containing the radical R$^8$ (where R$^8$ does not represent H), e.g.

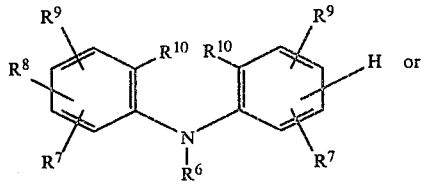

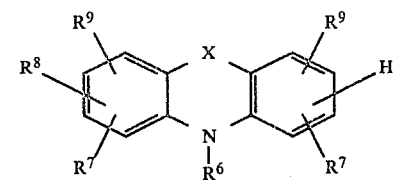

is introduced from the outset in a molar ratio corresponding to the required value of n, i.e. where n is intended on average to be the number 3, 1 mole of aromatic amine containing a substituent R$^8$ (which it is not representing H) is used per mole of aromatic amine in which R$^8$ is H.

The radical R$^6$ (when not representing H) may be introduced in the same way as the radical R$^8$ (not representing H). However, where R$^6$ does not represent alkyl or cycloalkyl, subsequent introduction under milder and modified conditions is recommended because these other radicals may possibly be detached again under the conditions of the synthesis reaction. For example a benzyl group may move from N into nucleus positions and, for this reason, is best subsequently attached to the nitrogen atom by alkylation under mild conditions, for example of the sodium salt of compounds III to V (substitution of the NH-hydrogen by Na) using benzylchloride.

For the same reasons, R$^6$ is also subsequently introduced when R$^6$ represents the radical

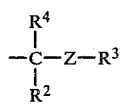

This radical is also formed by known methods such as condensing compounds corresponding to formulae III to (where R$^6$ represents H) with aldehydes and ketones of the formula R$^2$ COR$^4$ and compounds corresponding to the formula HZR$^3$ under mild conditions (for example at room temperature up to 100° C., in the presence of bases or even very small catalytic quantities of weak acids).

Subsequent substitution of the NH-hydrogen atom is advantageous in cases where the radical $R^6$ is intended to represent —CO—A—$R^2$. This is because a radical such as this deactivates the aromatic amines to a certain extent with respect to alkylating reagents so that unnecessarily rigorous conditions would be required for the synthesis reaction.

Compounds III to V in which $R^6$ represents H are converted into compounds III to V in which $R^6$=CO—A—$R^2$ by known acylation methods, for example using acid chlorides (Einhorn or Schotten-Baumann method), by thermal dehydrohalogenation or using acid anhydrides.

The reactants, aromatic amine and linking re-agent, are used in a molar ratio of from 5:1 to 1:5, preferably in a molar ratio of from 2:1 to 1:2 and, more preferably, in a molar ratio of from 1.5:1 to 1:1.5. Excess starting material may be removed by distillation at the working-up stage.

The reaction of the optionally-substituted parent amine compound with these compounds is carried out at temperatures in the range of from 50° to 300° C., and preferably at temperatures in the range of from 120° to 250° C., in the presence of acid catalysts. Acid catalysts in the context of the invention are strong acids having a pk-value, as measured in water, of less than 2, i.e., strong proton acids, such as hydrochloric acid, hydrobromic acid, sulfuric acid, sulfonic acid, p-toluene sulfonic acid, phosphoric acid, phosphorous acid, and trifluoroacetic acid. Further examples include Lewis acids, such as aluminum chloride, zinc chloride, iron-(III)chloride, titanium tetrachloride, boron trifluoride, antimony pentachloride, and adducts of these Lewis acids, such as $BF_3$-etherate, $BF_3$-hydrate, ion exchangers based on crosslinked sulfonated polystyrenes and acid-activated aluminas based on bentonite and montmorillonite.

These catalysts are used in quantities of from 0.1 to 20%, by weight, and preferably in quantities of from 0.2 to 10%, by weight, based on the reaction mixture. On completion of the reaction, they may be removed by neutralization and washing out or by filtration.

The reaction may be carried out in the presence or absence of solvents. Suitable solvents are inert to the reactants and should be readily removable. Examples of suitable solvents include aliphatic and aromatic hydrocarbons, such as decalin, petrol, benzene, toluene, xylene, cumene, and tetralin; aromatic halogenated hydrocarbons, such as chlorobenzene, dichlorobenzene and bromobenzene, thers, such as dioxane and anisole, esters, such as butylacetate or alcohols.

The reaction is generally carried out by heating the optionally-dissolved aromatic amine to the reaction temperature after addition of the catalyst, adding the alkylating compound and distilling off any product which may be released, such as water or alcohol. In many cases, there is no need for the reaction products to be worked-up. However, it is possible, as already described, to remove the catalyst, to distill off volatile constituents and to isolate the reaction product as a sump product, by precipitation or, in special cases, by crystallization from suitable solvents.

Aliphatic, cycloaliphatic, araliphatic, aromatic and heterocyclic polyisocyanates of the type described, for example, by W. Siefken in Justus Liebigs Annalen der Chemie, 562 pages 75 to 136 may be used as starting components for producing the polyurethanes. For example, polyisocyanates corresponding to the formula: $Q(NCO)_n$ wherein n=2—4, preferably 2, and Q represents an aliphatic hydrocarbon radical containing from 2 to 18, preferably from 6 to 10, carbon atoms; a cycloaliphatic hydrocarbon radical containing from 4 to 15, preferably from 5 to 10, carbon atoms; an aromatic hydrocarbon radical containing from 6 to 15, preferably from 6 to 13, carbon atoms; or an araliphatic hydrocarbon radical containing from 8 to 15, preferably from 8 to 13, carbon atoms may be used. Specifically, examples of such polyisocyanates include 1,4-tetramethylene diisocyanate, 1,6-hexamethylene diisocyanate, 1,12-dodecane diisocyanate, cyclobutane-1,3-diisocyanate, cyclohexane-1,3- and 1,4-diisocyanate, 1-isocyanato-3,3,5-trimethyl-5-isocyanato-methyl cyclohexane, 2,4- and 2,6-hexahydrotolylene diisocyanate and hexahydro-1,3- and/or 1,4-phenylene diisocyanate. Further examples of appropriate polyisocyanates include perhydro-2,4'- and/or -4,4'-diphenyl methane diisocyanate and their position and stereo isomer mixtures, 1,3- and 1,4-phenylene diisocyanate, 2,4- and/or 2,6-tolylene diisocyanate, diphenyl methane-2,4'- and/or -4,4'-diisocyanate and mixtures of these isomers, and naphthylene-1,5-diisocyanate.

According to the invention, it is also possible, for example, to use triphenyl methane-4,4',4''-triisocyanate, polyphenyl polymethylene polyisocyanates of the type obtained by condensing aniline with formaldehyde, followed by phosgenation, and described, for example, in British Pat. Nos. 874,430 and 848,671. M- and p-isocyanatophenyl sulfonyl isocyanates, perchlorinated aryl polyisocyanates, polyisocyanates containing carbodiimide groups, and norbornane diisocyanates are further examples of appropriate polyisocyanates. Polyisocyanates containing allophanate groups, isocyanurate groups, urethane groups, acylated urea groups, biuret groups or ester groups; or polyisocyanates produced by telomerization reactions; reaction products of any of the above-mentioned isocyanates with acetals; and polyisocyanates containing polymeric fatty acid esters according to U.S. Pat. No. 3,455,883 may be used. And, of course, it is also possible to use any mixtures of the above-mentioned polyisocyanates. A detailed list of suitable isocyanates, such as these, and their production methods is given on pages 8 to 11 of DE-OS No. 2,854,384.

In general, it is particularly preferred to use the commercially readily-available polyisocyanates, for example, 2,4- and 2,6-tolylene diisocyanate ("TDI"), polyphenyl polymethylene polyisocyanates of the type obtained by condensing aniline with formaldehyde, followed by phosgenation ("crude MDI"). Additionally, polyisocyanates containing carbodiimide groups, urethane groups, allophanate groups, isocyanurate groups, urea groups or biuret groups ("modified polyisocyanates"), particularly modified polyisocyanates of the type derived from 2,4- and/or 2,6-tolylene diisocyanate or from 4,4'- and/or 2,4'-diphenyl methane diisocyanate are also preferred. Finally, symmetrical and asymmetrical diphenyl methane diisocyanate derivatives substituted by methyl, ethyl or isopropyl groups are also suitable.

Compounds containing at least 2 isocyanate-reactive hydrogen atoms and having a molecular weight of generally from 400 to 10,000 are used as relatively high molecular weight polyol starting components. In addition to compounds containing amino groups, thio groups or carboxyl groups, compounds such as these include, preferably, compounds containing hydroxyl groups, particularly compounds containing from 2 to 8 hydroxyl groups, above all, those having molecular weights of from 600 to 6000, preferably from 800 to 5000. Examples of these include polyesters, polyethers, polythioethers, polyacetals, polycarbonates, and polyester amides containing at least 2, generally from 2 to 8, but preferably from 2 to 4 hydroxyl groups (of the type known for the production of homogeneous and cellular polyurethanes).

The polyesters containing hydroxyl groups suitable for use in accordance with the invention are, for example, reaction products of polyhydric, preferably dihydric and, optionally, trihydric alcohols with polybasic, preferably dibasic, carboxylic acids. Instead of using the free polycarboxylic acids, it is also possible to use the corresponding polycarboxylic acid anhydrides or corresponding polycarboxylic acid esters of lower alcohols or mixtures thereof for producing the polyesters. The polycarboxylic acids may be aliphatic, cycloaliphatic, aromatic and/or heterocyclic and may, optionally, be substituted, for example, by halogen atoms, and/or be unsaturated.

Examples of carboxylic acids such as these and their derivatives include adipic acid, sebacic acid, phthalic acid and its anhydrides, isophthalic acid, trimellitic acid, tetrahydrophthalic acid anhydride, hexahydrophthalic acid anhydride and tetrachlorophthalic acid anhydride. Additional examples include endomethylene tetrahydrophthalic acid anhydride, glutaric acid anhydride, maleic acid and its anhydride, fumaric acid, dimerized and trimerized unsaturated fatty acids, terephthalic acid dimethyl ester and terephthalic acid-bis-glycol ester. Suitable polyhydric alcohols include, for example, ethylene glycol, 1,2- and 1,3-propylene glycol, 1,4- and 2,3-butylene glycol, 1,6-hexane diol, neopentyl glycol, 1,4-bis-hydroxymethyl cyclohexane, 2-methyl-1,3-propane diol, glycerol, trimethylol propane, 1,2,6-hexane triol, 1,2,4-butane triol and trimethylol ethane. Further examples include pentaerythritol, quinitol, mannitol and sorbitol, formitol, methyl glycoside, diethylene glycol, triethylene glycol, tetraethylene glycol and higher polyethylene glycols, di-, tri- and tetra-propylene glycol and higher polypropylene glycols, di-, tri-, and tetra-butylene glycol and higher polybutylene glycols.

The polyesters thus produced may contain terminal carboxyl groups and polyesters of lactones, for example, ε-caprolactone, or of hydroxy carboxylic acids, for example, ω-hydroxy caproic acid, may also be used.

The polyethers containing at least 2, generally 2 to 8, and preferably 2 to 3, hydroxyl groups suitable for use in accordance with the invention are also known. These polyethers may be obtained, for example, by polymerizing epoxides, such as ethylene oxide, propylene oxide, butylene oxide, tetrahydrofuran, styrene oxide or epichlorohydrin on their own, for example, in the presence of Lewis catalysts, such as $BF_3$. They may also be obtained by the addition of these epoxides, preferably ethylene oxide and propylene oxide, in admixture or successively, with starter components containing reactive hydrogen atoms, such as water, alcohols, ammonia or amines (for example, ethylene glycol, 1,3-propylene glycol or 1,2-propylene glycol, trimethylol propane, glycerol, sorbitol, 4,4'-dihydroxy diphenyl propane, aniline, ethanolamine or ethylene diamine). Sucrose polyethers and also formitol- or formose-started polyethers may also be used in accordance with the invention. In many cases, it is preferred to use polyethers which predominantly contain primary OH— groups (up to 90% by weight, based on all the OH— groups present in the polyether).

Polybutadienes containing OH— groups are also suitable for use in accordance with the invention.

Among suitable polythioethers, reference is made, in particular, to the condensation products of thiodiglycol or its own and/or with other glycols, dicarboxylic acids, formaldehyde, aminocarboxylic acids or amino alcohols.

Suitable polyacetals include, for example, the compounds obtainable from glycols, such as diethylene glycol, triethylene glycol, 4,4'-dioxethoxy diphenyl dimethyl methane, hexane diol and formaldehyde.

Suitable polycarbonates containing hydroxyl groups are known. These polycarbonates may be obtained, for example, by reacting diols, such as 1,3-propane diol, 1,4-butane diol and/or 1,6-hexane diol, with diaryl carbonates, for example, diphenyl carbonate, or phosgene.

The polyester amides and polyamides include, for example, the predominantly linear condensates obtained, for example, from polybasic saturated or unsaturated carboxylic acids or their anhydrides and polyhydric saturated or unsaturated amino alcohols, diamines, polyamines and mixtures thereof.

Polyhydroxyl compounds already containing urethane or urea groups, and optionally, modified natural polyols, such as castor oil or carbohydrates (for example, starch), may also be used. Addition products of alkylene oxides with phenol-formaldehyde resins, or even with urea-formaldehyde resins may also be used in accordance with the invention.

Before they are used in the polyisocyanate-polyaddition process, the above-mentioned polyhydroxyl compounds may be modified in various ways. A mixture of different polyhydroxyl compounds (for example, a polyether polyol and a polyester polyol) may be condensed by etherification in the presence of a strong acid to form a relatively high molecular weight polyol which is made up of different segments attached through ether bridges. It is also possible to introduce triazine groups, for example.

In some cases, it is of particular advantage to completely or partly convert the relatively high molecular weight polyhydroxyl compounds into the corresponding anthranilic acid esters containing terminal aromatic amino groups by reaction with isatoic acid anhydride.

Relatively high molecular weight compounds containing terminal amino groups are obtained by reacting NCO prepolymers with enamines, aldimines or ketimines containing hydroxyl groups, followed by hydrolysis. Further processes for producing relatively high molecular weight compounds containing terminal amino groups or hydrazide groups are described in U.S. Pat. No. 3,625,871.

According to the invention, it is also possible to use polyhydroxyl compounds containing high molecular weight polyadducts and polycondensates or polymers in finely dispersed or dissolved form. Polyhydroxyl compounds such as these are obtained, for example, by carrying out polyaddition reactions (for example, reactions between polyisocyanates and aminofunctional compounds) and polycondensation reactions (for example between formaldehyde and phenols and/or amines) in situ in the above-mentioned compounds containing hydroxyl groups. However, it is also possible to mix an aqueous polymer dispersion with a polyhydroxyl compound and subsequently to remove the water from the mixture.

Polyhydroxyl compounds modified by vinyl polymers of the type obtained, for example, by polymerizing styrene and acrylonitrile in the presence of polyethers, are also suitable for use in the process according to the invention. Plastics having particularly good flameproof properties are obtained by using polyether polyols modified by graft polymerization with vinyl phosphonic acid esters and, optionally, acrylonitrile or methacrylonitrile, acrylamide or methacrylamide or OH— functional acrylic or methacrylic acid esters.

Where modified polyhydroxyl compounds of the type mentioned above are used as starting component in the polyisocyanate-polyaddition process, polyurethane plastics having considerably improved mechanical properties are formed in many cases.

Representatives of the above-mentioned compounds used in accordance with the invention are described, for example, in High Polymers, Vol. XVI, "Polyurethanes, Chemistry and Technology", by Saunders and Frisch Interscience Publishers, New York/London, Vol. I, 1962, pages 32 to 42 and pages 44 to 54 and Vol. II, 1964, pages 5–6 and 198–199. They are also described in Kunststoff-Handbuch, Vol. VII, Vieweg-Hochtlen, Carl-Hanser-Verlag, Munich, 1966, for example, on pages 45 to 71, and particularly in German Offenlegungsschrift No. 2,854,834, pages 11-21. It is, of course, possible to use mixtures of the above-mentioned compounds containing at least two isocyanate-reactive hydrogen atoms and having a molecular weight of from 400 to 10,000, such as mixtures of polyethers and polyesters.

Suitable starting components also include relatively low molecular weight compounds containing at least two isocyanate-reactive hydrogen atoms and having a molecular weight of from 32 to 400. In this case, too, the compounds in question are compounds containing hydroxyl groups and/or amino groups and/or thiol groups and/or carboxyl groups (preferably compounds containing hydroxyl groups and/or amino groups) which serve as chain extenders or crosslinkers. These compounds, which may also be used in admixture, generally contain from 2 to 8, and preferably from 2 to 4, isocyanate-reactive hydrogen atoms.

Examples of compounds such as these include ethylene glycol, 1,2- and 1,3-propylene glycol, 1,4- and 2,3-butylene glycol, 1,5-pentane diol, 1,6-hexane diol, 1,8-octane diol, neopentyl glycol, 1,4-bis-hydroxymethyl cyclohexane, 2-methyl-1,3-propane diol and dibromobutene diol. Suitable compounds include glycerol, trimethylol propane, 1,2,6-hexane triol, trimethylol ethane, pentaerythritol, quinitol, mannitol and sorbitol, castor oil, diethylene glycol, triethylene glycol, tetraethylene glycol and higher polyethylene glycols. Further examples include di-, tri- and tetra-propylene glycol and higher polypropylene glycols, di-, tri- and tetra-butylene glycol, higher polybutylene glycols (in each case having a molecular weight of up to 400), 4,4'-dihydroxy diphenyl propane, dihydroxy methyl hydroquinone, ethanolamine, diethanolamine, N-methyl diethanolamine, triethanolamine and 3-aminopropanol.

Still other low molecular weight polyols suitable for the purposes of the invention are mixtures of hydroxy aldehydes and hydroxy ketones ("formose") or the polyhydric alcohols obtained therefrom by reduction ("formitol"), advantageously in combination with aminoplast formers and/or phosphites. Solutions of polyisocyanate polyaddition products, particularly solutions of polyurethane ureas containing ionic groups and/or solutions of polyhydrazodicarbonamides in low molecular weight polyhydric alcohols may also be used as polyol component in accordance with the invention.

Aliphatic diamines suitable for use in accordance with the invention are, for example, ethylene diamine, 1,4-tetramethylene diamine, 1,11-undecamethylene diamine, 1,12-dodecamethylene diamine, p-xylylenediamine, bis-(3-aminopropyl)methylamine and mixtures thereof; or cycloaliphatic diamines, such as 1-amino-3,3,5-trimethyl-5-aminomethyl cyclohexane ("isophorone diamine"), 2,4- and/or 2,6-hexahydrotolylene diamine, perhydro-2,4'- and/or 4,4'-diamino-diphenyl methane, diamino-perhydroanthracenes or mixtures of their position and/or stereo isomers. Also, cycloaliphatic triamines according to German Offenlegungsschrift No. 2,614,244 are also suitable. It is also possible, in accordance with the invention, to use hydrazine and substituted hydrazines, and also acid dihydrazides, for example, carbodihydrazide, oxalic acid dihydrazide, the dihydrazides of malonic acid, adipic acid, β-methyl adipic acid, hydracrylic acid and terephthalic acid. Additionally, semicarbazido alkylene hydrazides, such as, for example, β-semicarbazido propionic acid hydrazide, semicarbazido alkylene carbazinic esters, such as, for example, 2-semicarbazido ethyl carbazinic ester or even aminocarbazide compounds such as, for example, β-aminoethyl semicarbazido carbonate may also be used. To control their reactivity, the amino groups may be completely or partly blocked by aldimine or ketimine groups.

Examples of aromatic diamines include bisanthranilic acid esters; 3,5- and 2,4-diaminobenzoic acid esters; the diamines containing ester groups described in German Offenlegungsschrift Nos. 1,803,635, 2,040,650 and 2,160,589; the diamines containing ether groups according to German Offenlegungsschrift Nos. 1,770,525 and 1,809,172; and 2-halogen-1,3-phenylene diamines, optionally substituted in the 5-position. Further examples include 3,3'-dichloro-4,4'-diaminodiphenyl methane, tolylene diamine, 4,4'-diaminodiphenyl methane, 4,4'-diaminodiphenyl disulfides, diaminodiphenyl dithio ethers, aromatic diamines substituted by alkyl thio groups, diamino-benzene phosphonic acid esters, aromatic diamines containing sulfonate or carboxylate groups, and the high-melting diamines described in German Offenlegungsschrift No. 2,635,400. Examples of aliphatic-aromatic diamines are the aminoalkyl thioanilines.

According to the invention, other suitable chain extenders include such compounds as 1-mercapto-3-aminopropane; optionally substituted amino acids, for example, glycine, alanine, valine, serine and lysine; and optionally substituted dicarboxylic acids, for example, succinic acid, adipic acid, phthalic acid, 4-hydroxy phthalic acid and 4-aminophthalic acid.

In addition, isocyanate-monofunctional compounds may be used as so-called chain terminators in proportions of from 0.01 to 10%, by weight, based on polyurethane solids. Monofunctional compounds such as these include, for example, monoamines, such as butyl and dibutylamine, stearylamine, N-methyl stearylamine, pyrrolidine and cyclohexylamine; and monoalcohols, such as butanol, 2-ethyl hexanol, cyclohexanol and ethylene glycol monoethyl ether.

Other low molecular weight polyols having a molecular weight of up to 400 which may be used in accordance with the invention include ester diols, for example, δ-hydroxybutyl-ε-hydroxycaproic acid ester, ω-hydroxyhexyl-γ-hydroxybutyric acid ester, adipic acid-bis-(β-hydroxyethyl)-ester and terephthalic acid-bis-(β-hydroxyethyl)-ester; and diol urethanes, for example, 1,6-hexamethylene-bis-(β-hydroxyethyl urethane) or 4,4'-diphenylmethane-bis-(δ-hydroxybutyl urethane). Additionally, diol ureas, such as 4,4'-diphenyl methane-bis-(β-hydroxyethyl urea) or the compound

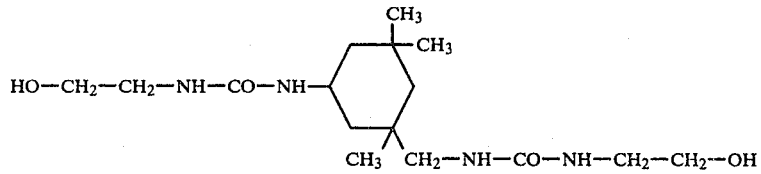

may also be used.

For certain purposes, it is of advantage to use polyols containing sulfonate and/or phosphonate groups (see, German Offenlegungsschrift No. 2,719,372), preferably the adduct of bisulfite with 1,4-butane diol or its alkoxylation products. Generally, these low molecular weight compounds having molecular weights of from 32 to 400 are described, in detail, in DE-OS No. 2,854,384, for example, on pages 20 to 26, where further examples are mentioned.

It is also possible to use known catalysts, for example, tertiary amines, such as triethylamine, N-methyl morpholine, tetramethyl ethylene diamine, 1,4-diazabicyclo-(2,2,2)-octane, bis-(dimethylaminoalkyl)-piperazines, dimethyl benzylamine, 1,2-dimethyl imidazole, monocyclic and bicyclic amidines, bis-(dialkylamino)-alkyl ethers and tertiary amines containing amide groups (preferably formamide groups). Suitable catalysts include also known Mannich bases of secondary amines, and aldehydes, or ketones. According to the invention, it is preferred to use organometallic compounds, particularly organo tin compounds as catalysts. In addition to sulfur-containing compounds, such as di-n-octyl tin mercaptide, preferred organo tin compounds include tin(II)salts of carboxylic acids, such as tin(II)acetate, tin(II)ethyl hexoate and tin(IV)compounds, for example, dibutyl tin dichloride, dibutyl tin diacetate, dibutyl tin dilaurate and dibutyl tin maleate.

All of the above-mentioned catalysts may of course be used in the form of mixtures. Further representatives of catalysts which may be used in accordance with the invention, and information on the way in which they work can be found in Kunststoff-Handbuch by Vieweg and Hochtlen, Vol. VII, Carl-Hanser-Verlag, Munich, 1966, for example, on pages 96 to 102 and in German Offenlegungsschrift No. 2,854,384.

Inorganic or organic substances may be used as blowing agents, particularly such compounds as methylene chloride, chloroform, vinylidene chloride, monofluorotrichloromethane, chlorodichlorodifluoromethane, as well as air, $CO_2$ or nitric oxide. More examples of blowing agents and information on their use may be found in Kunststoff-Handbuch by Vieweg and Hochtlen, Carl-Hanser-Verlag, Munich, 1966, for example, on pages 108 and 109, 453 to 455 and 507 to 510.

Surface-active additives, such as emulsifiers and foam initiators may be used in the normal way also. Examples of suitable emulsifiers include sodium salts of castor oil sulfonates or salts of fatty acids with amines such as diethyl amine oleate, and alkali or ammonium salts of sulfonic acids, such as dodecyl benzene sulfonic acid or dinaphthyl methane disulfonic acid.

Suitable foam stabilizers include, preferably, polyether siloxanes, particularly water-soluble types may be used. Reaction retarders, for example, acid-reacting compounds, such as hydrochloric acid, chloroacetic acid or organic acid halides, and known cell regulators, such as paraffins or fatty alcohols or dimethyl polysiloxanes may be used. Finally, pigments or dyes and/or known flameproofing agents and stabilizers against the effects of ageing and weather, plasticizers, fungistatic and/or bacteriostatic compounds and fillers may also be used. Information on these additives and auxiliaries and possibilities for the production of foams may be found in German Offenlegungsschrift No. 2,854,384, pages 26 to 31, and in the literature cited there.

The foams may be produced in the usual way both as free raise foams and as molded foams. The foams may, of course, also be produced by block foaming, by the known laminator process or by any other known method for producing foams.

The invention is further illustrated, but is not intended to be limited by the following examples in which all parts and percentages are by weight unless otherwise specified.

EXAMPLES

Production examples for the stabilizers

EXAMPLE 1

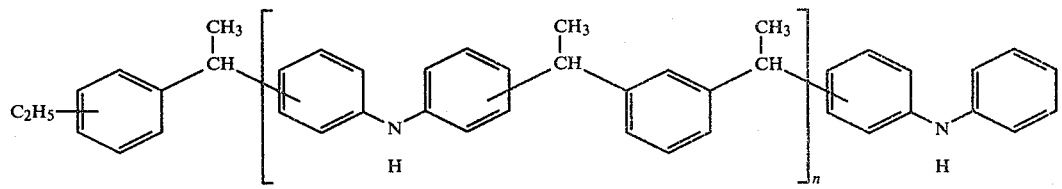

507 g (3 moles) of diphenylamine and 10 g of acid-activated alumina (Tonsil ® Optimum) are heated with stirring, under nitrogen, to 145°–150° C., followed by the dropwise addition, over a period of 3 hours, of 217 g of technical grade divinylbenzene (consisting of 61% of m- and p-divinylbenzene and 39% of ethylvinylbenzene). The reaction mixture is then kept at 150° C. for 1 hour. While it is still hot, the reaction mixture is press-filtered under nitrogen, then the filter cake is washed with hot xylene and press-filtered. The combined filtrates are concentrated by distillation and evaporation in vacuo and freed from volatile constituents up to a sump temperature of 190° C./14 mbar. The compound depicted above is obtained in the form of a light brown, highly viscous resin (620 g) with a molecular weight of 1800 (according to gel chromatography analysis). n is about 5, with some parts of lower values of n in the mixture.

EXAMPLE 2

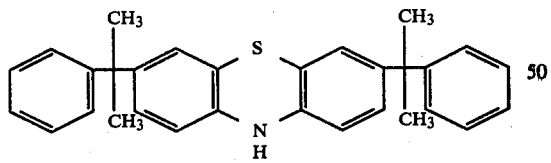

A mixture of 338 g (2 moles) of diphenylamine, 194 g (1 mole) of α,α'-dihydroxy-m-/p-diisopropylbenzene (molar ratio 3:2) and 10 g of acid-activated alumina is heated with stirring under nitrogen. Beyond a sump temperature of 120°–125° C., water distills over azeotropically and is distilled off at a continuously-increasing temperature. Finally, the reaction mixture is kept at 180° C. for 3 hours. After cooling to 100° C., it is diluted with toluene and press-filtered while still hot. After the filter cake has been washed and the combined filtrates concentrated by evaporation up to a sump temperature of 190° C./15 mbar, 480 g of the depicted compound are left in the form of a brown, soft resin, practically no solvents remaining in the product.

EXAMPLE 3

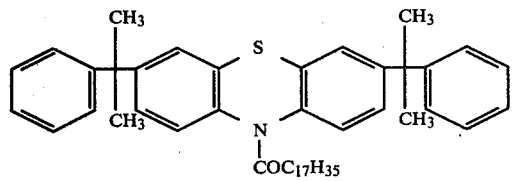

1000 g of phenothiazine, 1000 ml of xylene and 100 g of acid-activated alumina are heated with stirring, under nitrogen, to 180° C., some of the xylene being distilled off. 1190 g of α-methylstyrene are then added dropwise over a period of 3 hours, after which the reaction mixture is kept at 180° C. for 15 to 30 minutes. After dilution with 2 liters of xylene, the reaction mixture is press-filtered while still hot, washed with xylene and the still hot, clear filtrate is diluted with 2.5 liters of ligroin and left to cool, with stirring, in a nitrogen atmosphere. After filtration under suction, washing with xylene/ligroin and drying, 1750 g of the depicted compound are left in the form of pale yellow crystals melting at 129° to 133° C.

EXAMPLE 4

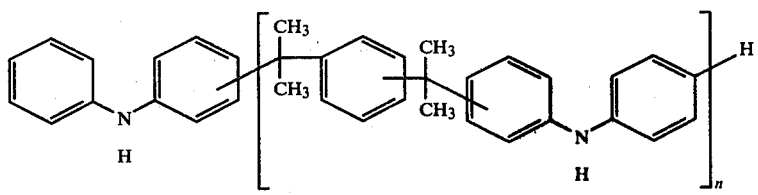

63 g (0.14 mole) of the compound of Example 3 are boiled under reflux for 1 hour with 29 g (0.29 mole) of acetanhydride in 150 ml of xylene and subsequently concentrated by evaporation to a sump temperature of 120° C./13 mbar. The depicted compound is obtained in the form of a brittle resin of which the NMR spectrum and elemental analysis agree with the indicated structure.

EXAMPLE 5

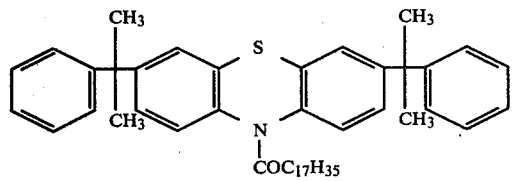

87 g (0.2 mole) of the compound of Example 3, and 63 g (0.2 mole) of stearic acid chloride are slowly heated, under nitrogen, with stirring, with hydrogen chloride being given off beyond 90°–100° C. The main reaction is over after 3 to 4 hours at 100° to 120° C. To remove hydrogen chloride, nitrogen is passed through for 2 hours at 100°–120° C. 138 g of the title compound are obtained in the form of a light brown resin.

EXAMPLE 6

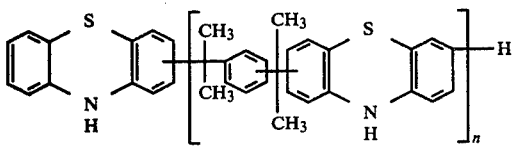

100 g (0.5 mole) of phenothiazine are dissolved with stirring, under nitrogen, and refluxed in 200 ml of xylene. 5 g of acid-activated alumina are added and xylene is distilled off in such a quantity that the sump temperature amounts to 160°–170° C. 97 g (0.5 mole) of α,α'-dihydroxy-m/p-diisopropylbenzene (molar ratio 3:2) are then introduced in portions and water is azeotropically removed from the circut. When no more water distills over, the reaction mixture is kept at 160° C. for about another 3 hours, filtered in a pressure filter and the filtrate is concentrated by evaporation up to a sump temperature of 190° C./30 mbar. A brown brittle resin (171 g) is obtained.

EXAMPLE 7

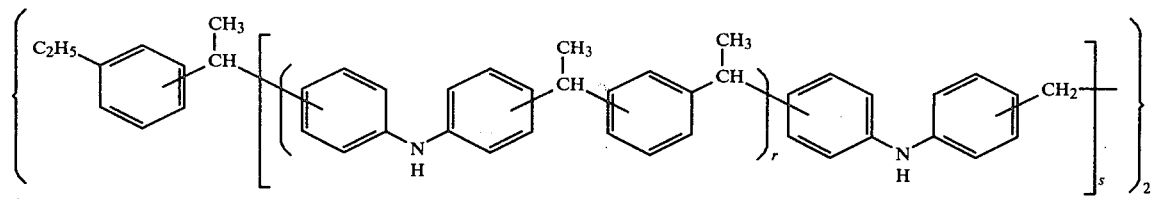

100 g of the compound of Example 1 are dissolved with stirring under nitrogen in isopropanol and the resulting solution is heated under reflux with 3 ml of concentrated hydrochloric acid and 12 ml of 35% formalin which has been added dropwise thereto. The precipitated deposit is dissolved by the addition of xylene. After refluxing for 2 additional hours, the phases are separated, the organic phase is washed with excess dilute sodium hydroxide then washed three times with water, filtered and concentrated by evaporation up to a sump temperature of 160° C./20 mbar. A highly viscous, brown resin is obtained, turning brittle on cooling (102 g).

EXAMPLE 8

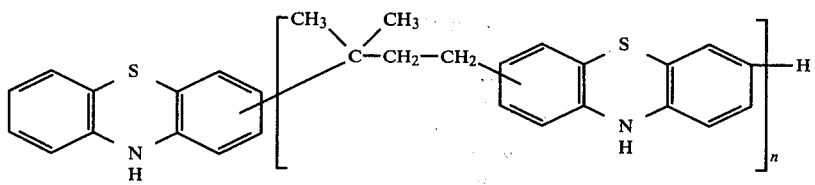

A mixture of 199 g (1 mole) of phenothiazine and 100 ml of xylene are heated with stirring, under nitrogen, to 150°–160° C. and 20 g of acid-activated alumina (Tonsil Optimum) are added to the clear solution. 68 g (1 mole) of isoprene are then added over a period of 4 hours from a cooled dropping funnel. After standing for 1 hour at 150° to 160° C., the reaction mixture is diluted with xylene and filtered in a pressure filter. After concentration by evaporation to a sump temperature of 190° C./18 mbar, the filtrate is 250 g of a brown resin.

EXAMPLE 9

100 g of the compound of Example 8 in 100 ml of xylene are reacted with 10 g of α-methyl styrene over a period of 4 hours with stirring, under nitrogen, at 150° C. in the presence of 2 g of acid-activated alumina. After filtration and concentration by evaporation, 110 g of a brown brittle resin remain.

EXAMPLE 10

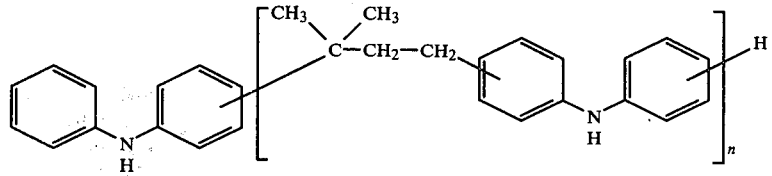

169 g (1 mole) of diphenylamine and 20 g of acid-activated alumina are heated with stirring, under nitrogen, to 180° C., followed by the addition, over a period of 2 to 3 hours, of 68 g (1 mole) of isoprene from a cooled dropping funnel. After 2 hours at 180° C., the reaction mixture is diluted with xylene, filtered and concentrated by evaporation to a sump temperature of 150° C./30 mbar. 195 g of a brown resin with a molecular weight of approximately 3200 (as determined by gel chromatography) are obtained.

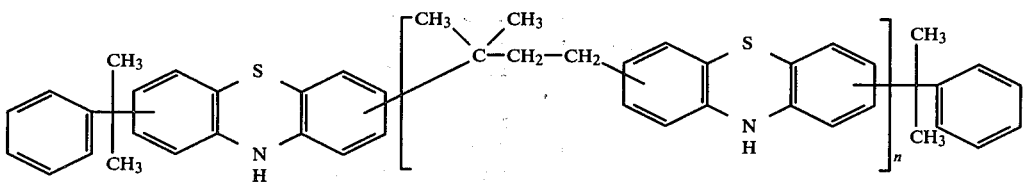

EXAMPLE 11

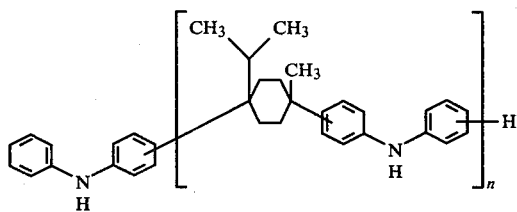

136 g (1 mole) of limonene are added dropwise over a period of 2 hours with stirring, under nitrogen, at 175°-180° C. to a mixture of 169 g (1 mole) of diphenylamine and 20 g of acid-activated alumina. After 2 hours at 190° C., the reaction mixture is diluted with xylene, filtered and concentrated by evaporation to a sump temperature of 190° C./10 mbar. 302 g of a pale yellow resin remain.

EXAMPLE 12

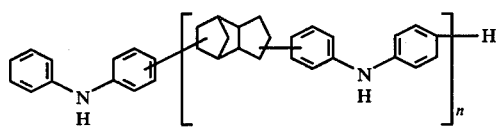

The procedure is as described in Example 11, except that 132 g (1 mole) of dicyclopentadiene are used instead of 136 g of limonene. 295 g of a brown resin are obtained.

EXAMPLE 13

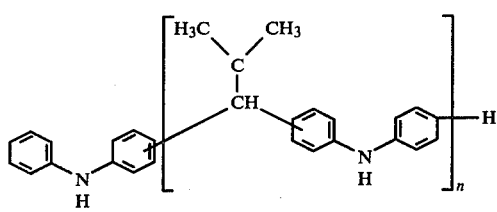

A mixture of 169 g (1 mole) of diphenylamine and 20 g (0.2 mole) of concentrated hydrochloric acid is heated to 190°-200° C., with water distilling off. 70 to 75 g of isobutyraldehyde is then added dropwise to the hot melt over a period of 3 to 4 hours with separation of the water formed. After 1 hour at 200° to 210° C., the reaction mixture is cooled, dissolved in toluene, and alkalized with 0,3 mol of a 10% ammonia solution. The organic phase is separated off, washed with H₂O and concentrated by evaporation in a water jet vacuum up to a sump temperature of 210° C./17 mbar. 160 g of a brown resin remain.

EXAMPLE 14

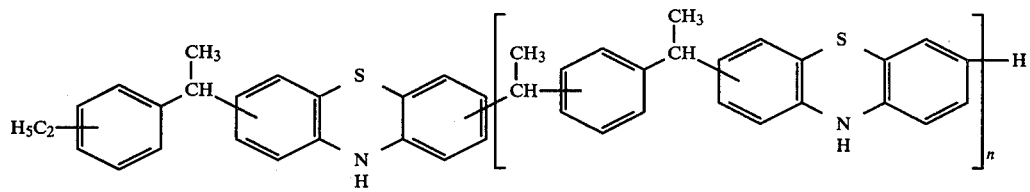

199 g (1 mole) of phenothiazine and 20 g of acid-activated alumina in 100 ml of xylene are heated, under nitrogen, to 160°-170° C., a little xylene being distilled off. 73 g of technical grade divinylbenzene (61% m/p-divinylbenzene and 39% ethylvinylbenzene) are then added dropwise, with stirring, over a period of 2 hours. The reaction mixture is kept at 170° C. for 1 hour and then filtered and concentrated by evaporation, leaving 265 g of a brown resin containing molecular species having a molecular weight 2700 (values of n between 2 and 8) (as determined by gel chromatography).

EXAMPLE 15

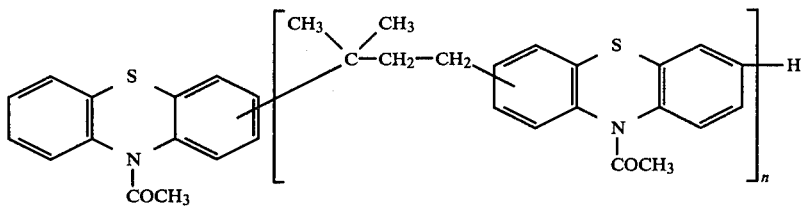

100 g (0.44 mole) of the compound of Example 8 are reacted with stirring, under nitrogen, at 134°-155° C. with 87 g (0.88 mole) of acetanhydride, acetic acid being distilled off through a short Vigreux column. Finally, excess acetanhydride is distilled off in a water jet vacuum at a sump temperature of 170° C./20 mbar. 118 g of a greenish-brown glass-like resin are obtained, its NMR-spectrum agreeing with the depicted compound.

EXAMPLE 16

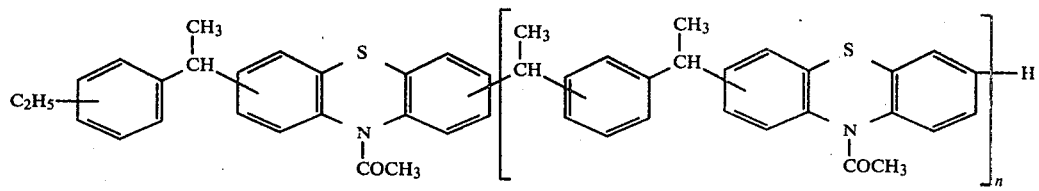

100 g of the compound of Example 14 are reacted with 76 g of acetanhydride as described in Example 15, giving 117 g of a glass-like greenish resin.

EXAMPLE 17

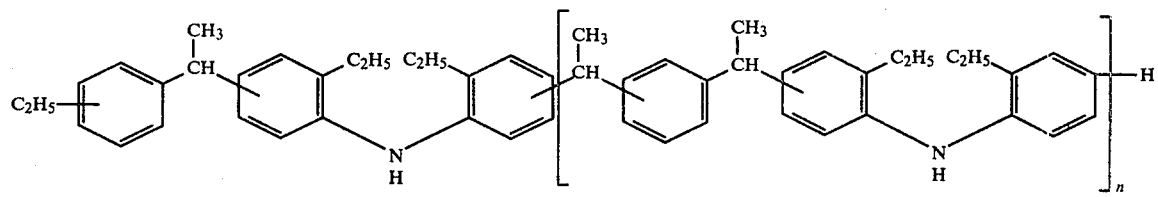

113 g of 2,2'-diethyldiphenylamine and 5 g of acid-activated alumina (Tonsil Optimum) are heated under nitrogen, with stirring, to 140°–145° C. followed by the dropwise addition over a period of 1 hour of 81 g of technical grade divinylbenzene (cf, Example 1). After 2.5 hours at 140° C., the reaction mixture is diluted with xylene, filtered and concentrated by evaporation, leaving 165 g of a pale, brown resin.

EXAMPLE 18

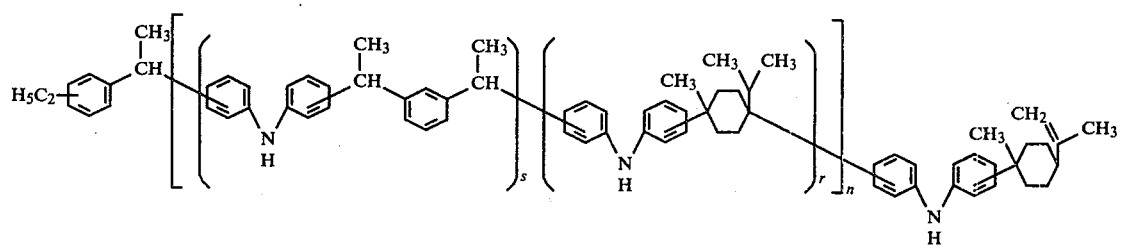

10 g of isoprene are added dropwise over a period of 4 hours with stirring, under nitrogen, at 180° C. to 100 g of the product of Example 1 and 3 g of acid-activated alumina in 100 g of o-dichlorobenzene. After another 30 minutes, the mixture is filtered and concentrated by evaporation to a sump temperature of 180° C./10 mbar, leaving 108 g of a light brown resin containing molecular species with molecular weights of up to approximately 2500 (as determined by gel chromatography).

EXAMPLE 19

The procedure is as in Example 18, except that instead of isoprene, 30 g of limonene are added dropwise over a period of 1 hour, followed by stirring the mixture for 2 hours at 180° C. Working up gives 120 g of a brittle, brown resin containing molecular species having molecular weights of up to about 2500 (as determined by gel chromatography).

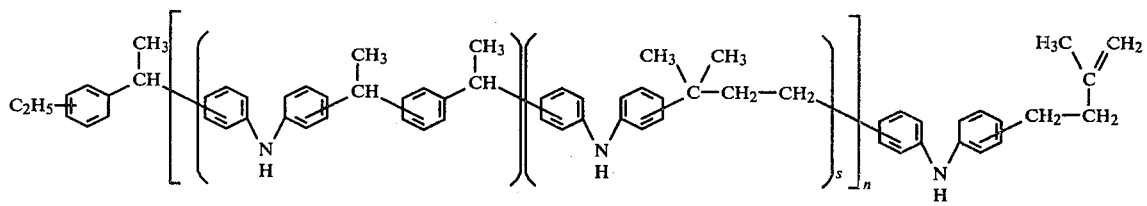

EXAMPLE 20

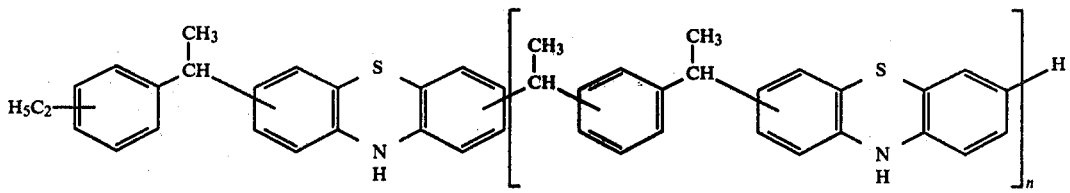

26 g of concentrated hydrochloric acid are added with stirring, under nitrogen, to a mixture of 199 g (1 mole) of phenothiazine and 200 ml of xylene, after which water and then xylene are azeotropically distilled off until the sump temperature reaches 160° C. 164 g of technical grade divinylbenzene (see Example 1) are added dropwise to the resulting melt over a period of 3.5 hours, after which the melt is kept at 160° C. for 2 hours. The melt is dissolved in xylene and washed at 80°

50 g of styrene are added dropwise over a period of 30 minutes with stirring, under nitrogen, at 150° C. to 100 g of the product of Example 12 and 5 g of acid-activated alumina, after which the reaction mixture is kept at 150° C. for 3 hours. After filtration and concentration by vaporation up to a sump temperature of 170° C./20 mbar, 124 g of a light brown resin remain.

EXAMPLE 23

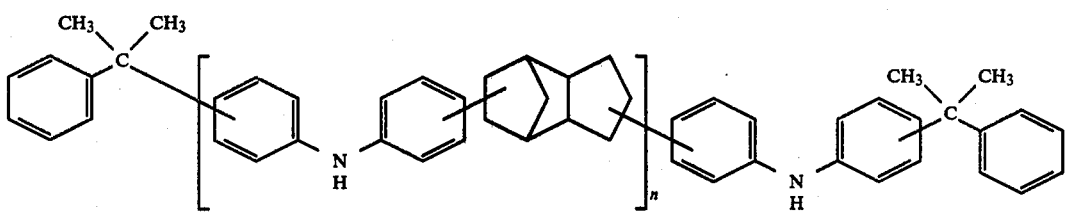

to 90° C. with dilute sodium hydroxide until it shows a basic reaction and then washed with water. The organic phase is concentrated by evaporation up to a sump temperature of 170° C./25 mbar. 365 g of a yellow- The procedure is as in Example 22, except that 50 g of α-methylstyrene are used instead of styrene. 118 g of a light brown, brittle resin are otained.

EXAMPLE 24

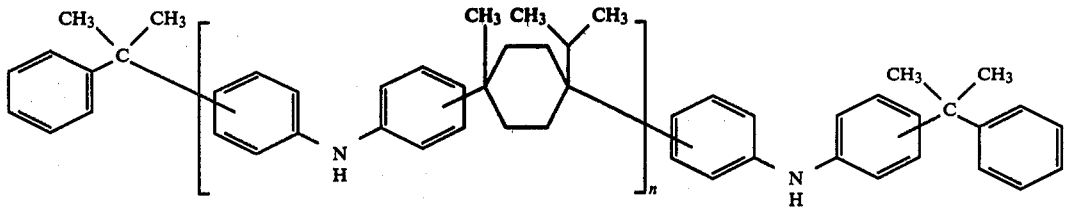

brown, glass-like resin are obtained.

EXAMPLE 21

The procedure is as described in Example 20, except that 5 g instead of 26 g of concentrated hydrochloric acid are used. The yield amounts to 315 g of a light brown resin.

EXAMPLE 22

100 g of the product of Example 11 and 5 g of acid-activated alumina are heated with stirring, under nitrogen, to 150° C., followed by the dropwise addition, over a period of 30 minutes, of 50 g of α-methylstyrene. After another 2 to 3 hours at 150° C., the mixture is filtered hot in a pressure filter and concentrated by evaporation to a sump temperature of 190° C./15 mbar, leaving 135 g of a yellow, brittle resin.

EXAMPLE 25

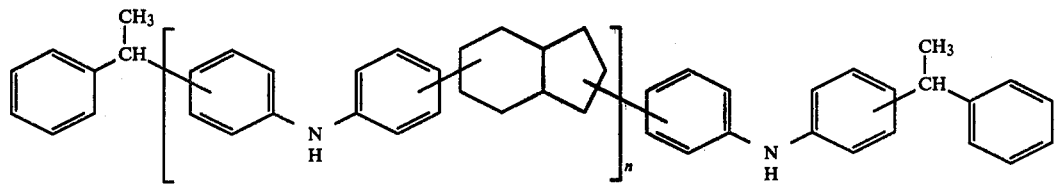

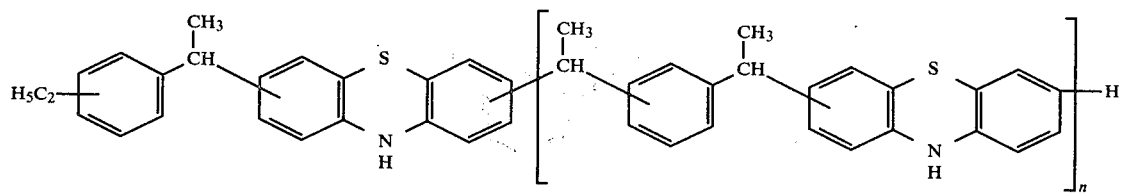

164 g of technical grade divinylbenzene (Example 1) are added dropwise over a period of 3 hours with stirring, under nitrogen, at 150° C. to a melt of 199 g (1 mole) of phenothiazine containing 2 g of acid-activated alumina, after which the reaction mixture is kept at 150°–160° C. for 4 hours, diluted with xylene, filtered while still hot and concentrated by evaporation to a sump temperature of 180° C./16 mbar. 320 g of a yellow-brown, glass-like resin are obtained.

EXAMPLE 26

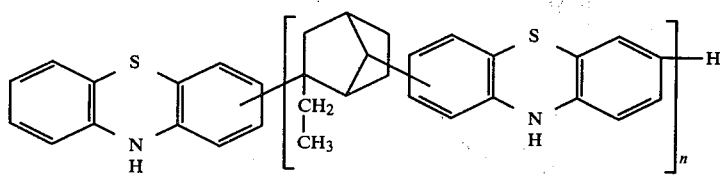

120 g (1 mole) of ethylene norbornene are added dropwise over a period of 3 hours with stirring, under nitrogen, at 180° C. to a melt of 199 g (1 mole) of phenothiazine containing 10 g of acid-activated alumina, followed by stirring for 2 hours at 180° C. After press-filtering and concentration by evaporation to a sump temperature of 180° C./20 mbar, 300 g of a brown resin result.

EXAMPLE 27

132 g (1 mole) of dicyclopentadiene are added dropwise over a period of 2 hours with stirring, under nitrogen, at 160°–170° C. to a melt of 199 g (1 mole) of phenothiazine containing 10 g of acid-activated alumina and the resulting mixture is kept under the reaction conditions for 2 to 3 hours. After press-filtering and concentration by evaporation to a sump temperature of 190° C./0.6 mbar, 150 g of a brown, brittle resin remain.

EXAMPLE 28

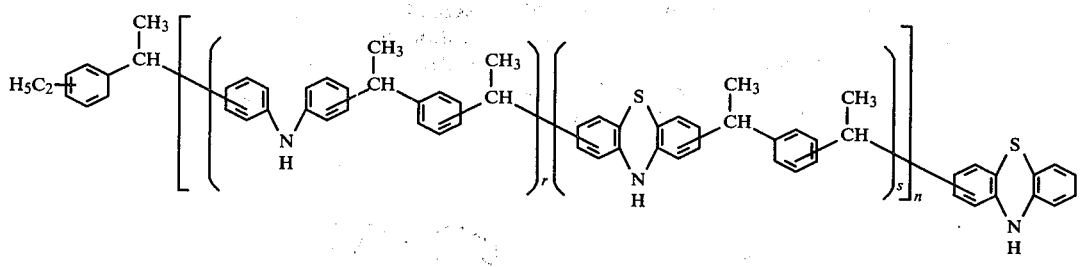

A mixture of 84.5 g (0.5 mole) of diphenylamine, 99.5 g (0.5 mole) of phenothiazine and 10 g of acid-activated alumina is heated under nitrogen, with stirring, to 150° C., followed by the dropwise addition, over a period of 3 hours, of 73 g of technical grade divinylbenzene (see Example 1). After another hour at 150° C., the mixture diluted with xylene, press-filtered while still hot and concentrated by evaporation up to a sump temperature of 150° C./10 mbar, leaving 238 g of a green-brown, brittle resin.

EXAMPLE 29

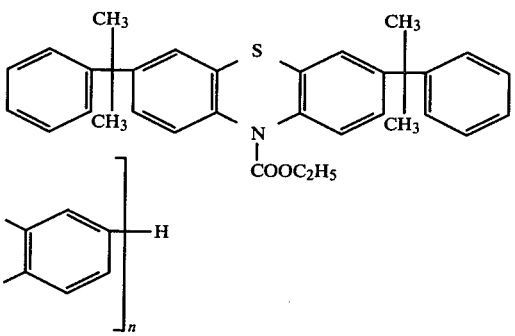

90 g of the compound of Example 3 and 22 g of chloroformic acid ethyl ester are slowly heated with stirring, under nitrogen, until hydrogen chloride is vigorously given off at 100° to 110° C. After about 1 hour, the evolution of gas stops almost completely, the mixture is heated to 120° C. and nitrogen is passed therethrough to remove the remaining hydrogen chloride. 103 g of a light green-grey, clear, brittle resin remain.

EXAMPLE 30

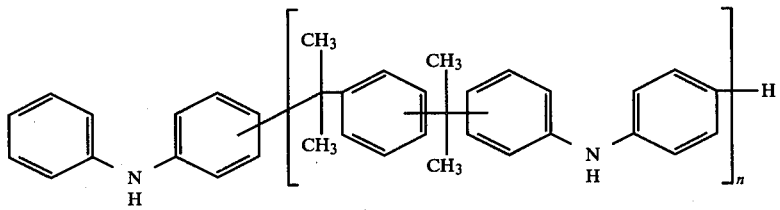

507 g (3 moles) of diphenylamine and 194 g (1 mole) of α,α′-dihydroxy-m/p-diisopropylbenzene (molar ratio 3:2) are melted and combined under nitrogen, followed by the addition of 60°–70° C. of 20 g of acid-activated alumina. The mixture is then slowly heated with stirring until H₂O is released beyond 110° C. After all the water (36 g in all) has passed over, the mixture is heated for another 2 hours from 160° to 180° C., filtered through a heated pressure filter and the monomers are distilled off at 8–10 mbar up to a sump temperature of 240° C. and a head temperature of 160° C. 451 g of a clear, brittle, pale light-brown resin are obtained.

EXAMPLE 31

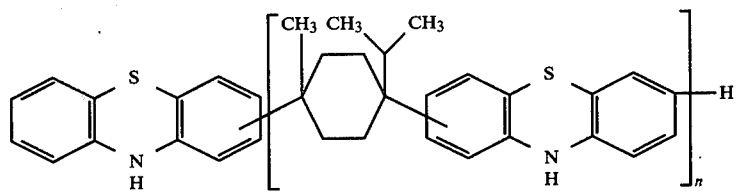

10 g of acid-activated fuller's earth are added, under nitrogen, at 180°–185° C. to a melt of 199 g (1 mole) of phenothiazine, followed by the dropwise addition over a period of 1 hour, with stirring, of 136 g (1 mole) of limonene. After stirring for another 2 hours at 180° C., the mixture is diluted with xylene, filtered through a pressure filter and the clear, yellow, filtrate is further concentrated by evaporation in a water jet vacuum up to a sump temperature of 190° C./25 mbar. 310 g of a yellow-brown, brittle resin containing molecular species with molecular weights of up to about 2800 (as determined by gel chromatography) remain.

EXAMPLE 32

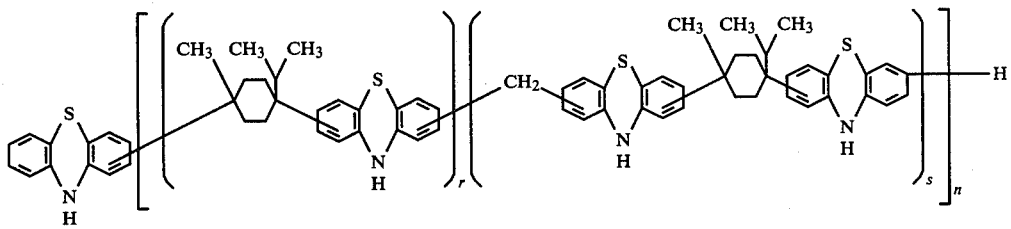

3 g of acid-activated alumina and 9 g of 35% formalin are added with stirring, under nitrogen, to 100 g of the product of Example 31 in 100 g of o-dichlorobenzene and the resulting mixture is refluxed for 2 hours. The sump temperature is increased to 180° C., while water is distilled off, and kept at that level for 2 hours, after which the mixture is filtered and concentrated by evaporation up to 200° C./18 mbar. 101 g of a light brown, brittle resin with molecular weights of up to 3500 (as determined by gel chromatography) results.

EXAMPLE 33

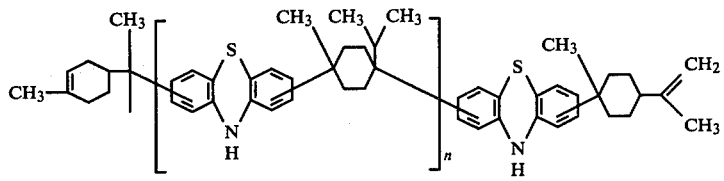

150 g (1.1 mole) of limonene are added dropwise over a period of 2 hours with stirring, under nitrogen, at 170°–180° C. to a mixture of 199 g (1 mole) of phenothiazine, 200 g of o-dichlorobenzene and 10 g of acid-activated alumina. The mixture is then left to react for 3 hours, filtered and concentrated by evaporation to a sump temperature of 200° C./9 mbar. 340 g of a yellow-brown, brittle resin containing molecular species with molecular weights of up to 3400 are obtained. Examples of the use of the stabilizer in the production of foams:

I General Test Procedure

Foams measuring 1.8 m (L) by 1.0 m (W) by approximately 1.2 m (H) were produced for the practical testing of the stabilizers according to the invention.

1%, by weight, of the optionally-powdered stabilizers were weighed into the particular polyether polyols, followed by heating (to a maximum of 80° C.), with continuous stirring, until the stabilizers had completely dissolved. After cooling, this stabilizer/polyether stock batch was added to the polyether polyol reaction mixture in a quantity such that concentrations of 0.1%, by weight, and 0.2%, by weight, respectively, of stabilizer result. The other components (foam stabilizers and amine catalysts) were weighed into a polyether polyol stock mixture and stirred at around 1800 r.p.m. This mixture of polyol and other components was then added to the polyether polyol reaction mixture (containing stabilizer) in situ (just before addition of the polyisocyanate), and the entire mixture was homogenized for 60 seconds at 1800 r.p.m. Tin catalyst and the water were then optionally stirred in over a period of 60 seconds at the same speed.

For addition of the polyisocyanate, the container accommodating the polyol mixture was introduced into a film-lined box having the inside dimensions desired of the final foam product (L=1.8 m, W=1.0 m, H=approximately 1.2 m). The necessary quantity of polyisocyanate was then mixed with the polyether polyol containing all the additives for about 10 seconds at around 1000 r.p.m., after which the reaction mixture was poured out just above the base of the film-lined box. The mixture foams and hardens to form the foam block. After about 24 hours, the foam blocks are cut up for the purpose of assessing core discoloration/core scorching.

The stabilizers according to the invention were used in three foam formulations, differing from one another in their water content (6.5 and 8.0% by weight) and in the type of catalyst used.

Formulation A 100 parts, by weight, of a trifunctional, trimethylolpropane-started polypropylene ether polyol having an OH number of 56 and prestabilized with 0.20%, by weight, of ionol;

1.5 parts, by weight, of a standard commercial polysiloxane polyalkylene glycol block copolymer as flexible-foam stabilizer;

0.15 part, by weight, of tin(II)octoate catalyst;

0.1 part, by weight, of a standard commercial amine catalyst mixture (Desmorapid ® PS 207, a product of Bayer AG);

6.5 parts, by weight, of water;

75.1 parts, by weight, of tolylene diisocyanate (mixture of 2,4- and 2,6-diisocyanatotoluene in a ratio of 80:20; NCO index=105); and 0.1 part, by weight, of the stabilizer to be tested.

Formulation B 100 parts, by weight, of a trifunctional polyether polyol (as in Formulation A);

1.5 parts, by weight, of a standard commercial polysiloxane polyalkylene glycol block copolymer as flexible-foam stabilizer;

0.15 part, by weight, of tin(II)octoate catalyst;

0.15 part, by weight, of a standard commercial amine activator (33% solution of triethylene diamine in dipropylene glycol);

0.3 part, by weight, of dimethyl ethanolamine;

6.5 parts, by weight, of water;

78.7 parts, by weight, of tolylene diisocyanate (a mixture of 2,4- and 2,6-diisocyanatotoluene in a ratio of 80:20; NCO index=110); and 0.1 part, by weight, of the stabilizer to be tested.

Formulation C 100 parts, by weight, of a trifunctional polyether polyol (as in Formulation A);

1.8 parts, by weight, of a standard commercial polysiloxane polyalkylene glycol block copolymer as flexible-foam stabilizer;

0.17 part, by weight, of tin(II)octoate catalyst;

0.2 part, by weight, of a standard commercial amine catalyst mixture (Desmorapid PS207);

8.0 parts, by weight, of water;

94.6 parts, by weight, of tolylene diisocyanate (as in Formulation B); and 0.1 part, by weight, of the stabilizer to be tested.

TABLE 1

| | | PU-foam assessment for core discoloration | | | | | |
|---|---|---|---|---|---|---|---|
| | | F + 0.1% by weight of dioctyl diphenylamine stabilizer (prior art) | | F + 0.1% by weight of stabilizer(s) according to the invention | | Stabilizer | Stabilizer Group |
| Practical Example No. | Formulation (F) | Visual Assessment | Brown Scale | Visual Assessment | Brown Scale | Example No.(s) | (general formula) |
| 35 | A | very heavy core discoloration | 7 | slight core discoloration | 2 | 3 | I |
| 36 | B | very heavy core discoloration | 7 | core discoloration | 4 | 3 | |
| 37 | C | self-ignition (SI) | SI | core discoloration | 5 | 3 | |
| 38 | A | very heavy core discoloration | 7 | core discoloration | 4 | 29 | II |
| 39 | B | very heavy core discoloration | 7 | core discoloration | 5 | 29 | |
| 40 | A | very heavy core discoloration | 7 | core discoloration | 4 | 5 | II |
| 41 | B | very heavy core discoloration | 7 | core discoloration | 5 | 5 | |
| 42 | A | very heavy core discoloration | 7 | slight core discoloration | 2 | 1 | III |
| 43 | B | very heavy core discoloration | 7 | slight core discoloration | 3 | 1 | |

TABLE 1-continued

| | | PU-foam assessment for core discoloration | | | | | |
|---|---|---|---|---|---|---|---|
| | | F + 0.1% by weight of dioctyl diphenylamine stabilizer (prior art) | | F + 0.1% by weight of stabilizer(s) according to the invention | | Stabilizer | Stabilizer Group |
| Practical Example No. | Formulation (F) | Visual Assessment | Brown Scale | Visual Assessment | Brown Scale | Example No.(s) | (general formula) |
| 44 | C | self-ignition | SI | core discoloration | 5 | 1 | |
| 45 | A | very heavy core discoloration | 7 | slight core discoloration | 2 | 2 | III |
| 46 | B | very heavy core discoloration | 7 | slight core discoloration | 3 | 2 | |
| 47 | C | self-ignition | SI | heavy core discoloration | 6 | 2 | |
| 48 | A | very heavy core discoloration | 7 | slight core discoloration | 2 | 10 | III |
| 49 | B | very heavy core discoloration | 7 | slight core discoloration | 3 | 10 | |
| 50 | C | self-ignition | SI | core discoloration | 5 | 10 | |
| 51 | A | very heavy core discoloration | 7 | no core discoloration | 0 | 14 | IV |
| 52 | B | very heavy core discoloration | 7 | no core discoloration | 0 | 14 | |
| 53 | C | self-ignition | SI | no core discoloration | 0 | 14 | |
| 54 | A | very heavy core discoloration | 7 | no core discoloration | 0 | 8 | IV |
| 55 | B | very heavy core discoloration | 7 | no core discoloration | 0 | 8 | |
| 56 | C | self-ignition | SI | no core discoloration | 0-1 | 8 | |
| 57 | A | very heavy core discoloration | 7 | no core discoloration | 0 | 6 | IV |
| 58 | B | very heavy core discoloration | 7 | no core discoloration | 0-1 | 6 | |
| 59 | C | self-ignition | SI | no core discoloration | 0-1 | 6 | |
| 60 | A | very heavy core discoloration | 7 | no core discoloration | 0 | 31 | IV |
| 61 | B | very heavy core discoloration | 7 | no core discoloration | 0 | 31 | |
| 62 | C | self-ignition | SI | no core discoloration | 0 | 31 | |
| 63 | A | very heavy core discoloration | 7 | no core discoloration | 0 | 28 | V |
| 64 | B | very heavy core discoloration | 7 | no core discoloration | 0 | 28 | |
| 65 | C | self-ignition | SI | slight core discoloration | 2 | 28 | |

NOTE:
According to the Brown Scale, 0 = no core discoloration
1-7 = increasing core discoloration from very slight to very heavy
SI = self-ignition

SUMMARY

The results of the individual stabilization tests (Practical Examples 35 to 65 in Table 1) demonstrate the extreme effectiveness of the stabilizers according to the invention.

With optimal protection against oxidation by the conventional and still-practiced method, heavy core discoloration is practically unavoidable in formulations having a relatively high water content. In the case of particularly critical formulations (i.e., formulation C), self-ignition of the foams is apparent. By contrast, the stabilizers according to the invention show considerably more favorable behavior. Using the stabilizer groups of general formulae I, III, IV and V, it is possible to stabilize the foams to such an extent that self-ignition is extremely unlikely. Of the preferred product groups III, IV and V, the stabilizers of group IV give particularly favorable results. Using these stabilizers, not only is it possible to virtually prevent self-ignition, it is also possible to substantially rule out core discoloration of the foams.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

We claim:

1. Stabilizer-containing reactive components for the production of polyurethane foams having little or no tendency toward core discoloration, which are based on polyisocyanates, polyols and optionally, water, blowing agents, catalysts, other stabilizers and standard additives, characterized in that said components contain, as stabilizers, monomeric and/or oligomeric derivatives of the diphenylamine series, including the phenothazine series, in stabilizing quantities of from 0.02 to 5%, by weight, of compounds corresponding to the formula:

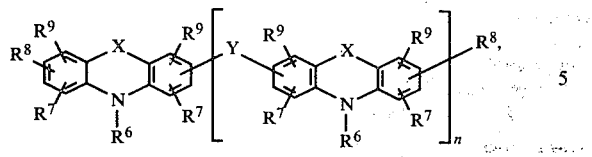

wherein
X represents a single bond, $>CH_2$, $\geqq CH$, $>S$, $>O$, $>NR^5$,

or $>POH$;
Y represents

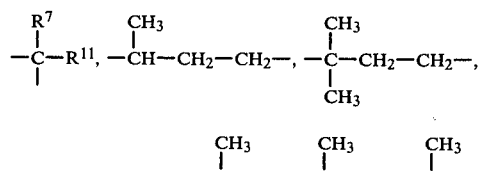

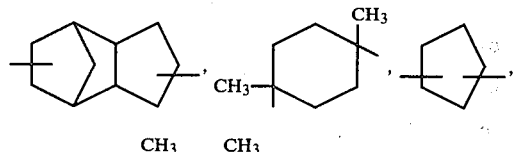

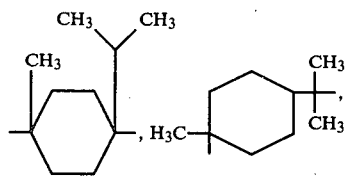

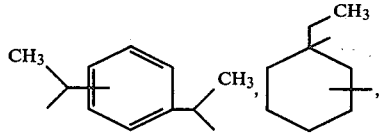

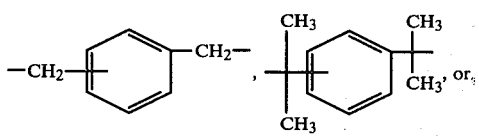

and, up to 60 mole percent, —S—, —CH$_2$—, —CH$_2$—S—CH$_2$— or —CH$_2$—O—CH$_2$—;
n represents an integer of from 1 to 29;
$R^6$ represents H, or a $C_1$–$C_{18}$-alkyl, a $C_5$–$C_{12}$-cycloalkyl, a $C_5$–$C_{12}$-cycloalkenyl, $C_7$–$C_{18}$-aralkyl which may optionally be substituted by OH—, SH—, ether, thioether, carbonic ester, carbonamide and carboxyl groups or which may be interrupted by such groups other than OH, SH and COOH— groups and olefinic double bonds,

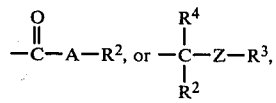

wherein
$R^2$, $R^3$ and $R^4$ may be the same or different and represents H, a $C_1$–$C_{12}$-alkyl, a $C_5$–$C_{12}$-cycloalkyl, a $C_5$–$C_{12}$-cycloalkenyl, or a $C_7$–$C_{12}$-aralkyl, in addition to which, $R^2$ represents optionally-substituted aryl and, together with $R^4$ and the central C-atom, may form a 5- to 12-member aliphatic ring;
Z represents O, S, NH, $NR^5$, wherein $R^5=R^2$, or a radical of the formula CO—A—$R^2$, wherein A is a single bond, S, O, NH or $NR^2$, but where $R^2$ does not form a ring with $R^4$, or Z together with $R^3$ also represents

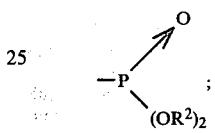

$R^7$ and $R^9$ may be the same or different and represent H, $CH_3$ or $C_2H_5$;
$R^8$ represents H, benzyl, styryl, α-methyl-styryl, tert.-butyl, tert.-amyl, isononyl, cyclohexyl, methyl cyclohexyl,

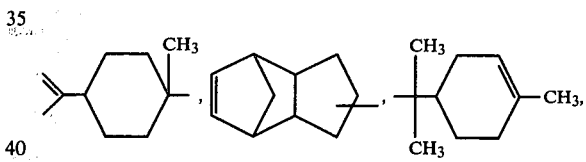

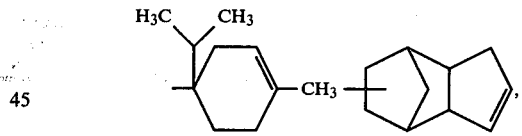

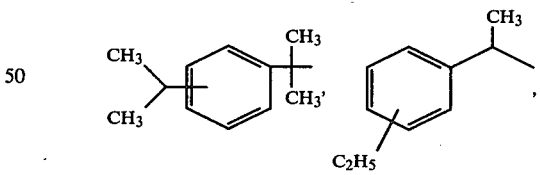

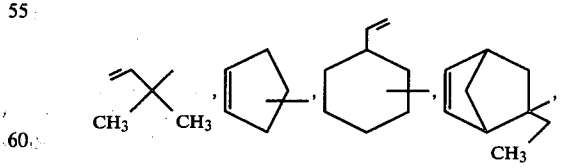

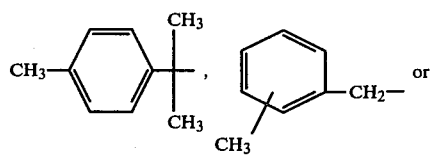

-continued

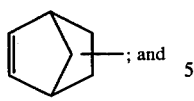; and $R^{11}$ represents a $C_1$–$C_7$-alkyl, cyclohexyl, cyclohexenyl or aryl.

2. Stabilizer-containing reactive components according to claim 1, characterized in that $R^5$, $R^6$, $R^7$, $R^8$ and $R^9$ represent H; and Y represents

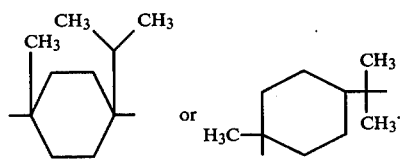

3. Compounds corresponding to the general formula

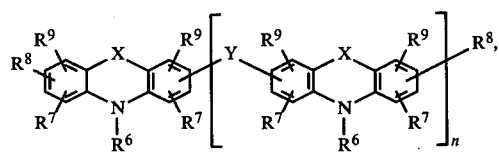

wherein
X represents a single bond, $>CH_2$, $\geq CH$, $>S$, $>O$, $>NR^5$,

or $>POH$;
Y represents

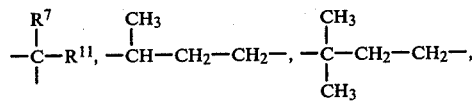

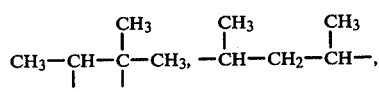

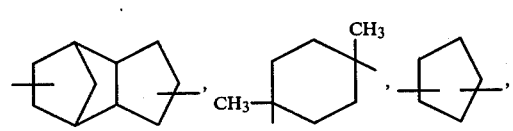

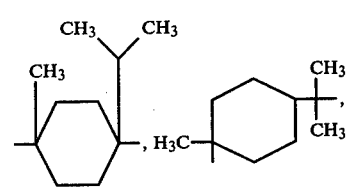

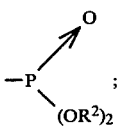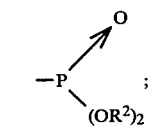

-continued

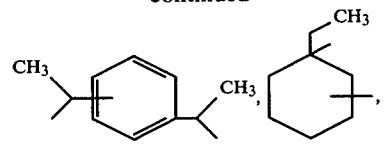

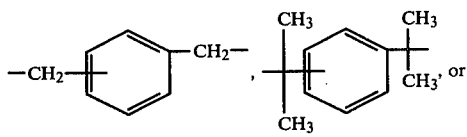

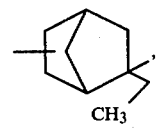

and, up to 60 mole percent, —S—, —CH$_2$—, —CH$_2$—S—CH$_2$— or —CH$_2$—O—CH$_2$—;
n represents an integer of from 1 to 29;
$R^6$ represents H, or a $C_1$–$C_{18}$-alkyl, a $C_5$–$C_{12}$-cycloalkyl, a $C_5$–$C_{12}$-cycloalkenyl, $C_7$–$C_{18}$-aralkyl which may optionally be substituted by OH—, SH—, ether, thioether, carbonic ester, carbonamide and carboxyl groups or which may be interrupted by such groups other than OH, SH and COOH— groups and olefinic double bonds,

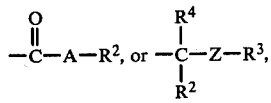

wherein
$R^2$, $R^3$ and $R^4$ may be the same or different and represents H, a $C_1$–$C_{12}$-alkyl, a $C_5$–$C_{12}$-cycloalkyl, a $C_5$–$C_{12}$-cycloalkenyl, or a $C_7$–$C_{12}$-aralkyl, in addition to which, $R^2$ represents optionally-substituted aryl and, together with $R^4$ and the central C-atom, may form a 5- to 12-member aliphatic ring;
Z represents O, S, NH, $NR^5$, wherein $R^5=R^2$, or a radical of the formula CO—A—$R^2$, wherein A is a single bond, S, O, NH or $NR^2$, but where $R^2$ does not form a ring with $R^4$, or Z together with $R^3$ also represents $$-P\begin{matrix}\nearrow O\\ \searrow (OR^2)_2\end{matrix};$$

$R^7$ and $R^9$ may be the same or different and represent H, CH$_3$ or C$_2$H$_5$;
$R^8$ represents H, benzyl, styryl, α-methyl-styryl, tert.-butyl, tert.-amyl, isononyl, cyclohexyl, methyl cyclohexyl,

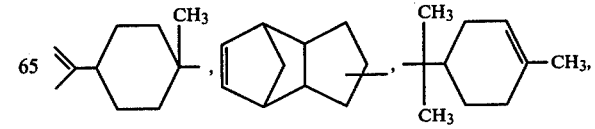

-continued

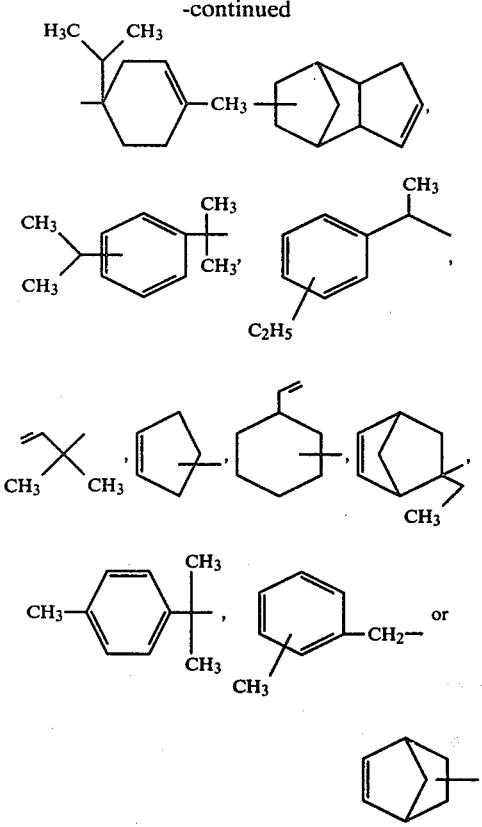

$R^{11}$ represents a $C_1$–$C_7$-alkyl, cyclohexyl, cyclohexenyl or aryl.

4. Compounds according to claim 3, characterized in that $R^5$, $R^6$, $R^7$, $R^8$ and $R^9$ represent H; and Y represents

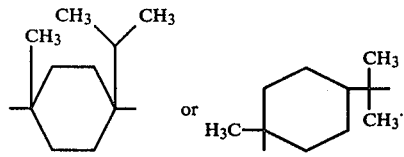

5. A process for the production of monomeric and/or oligomeric mixtures of the compounds corresponding to the formula:

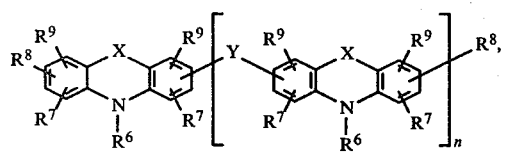

wherein

X represents a single bond, $>CH_2$, $\geq CH$, $>S$, $>O$, $>NR^5$,

or $>POH$;

Y represents

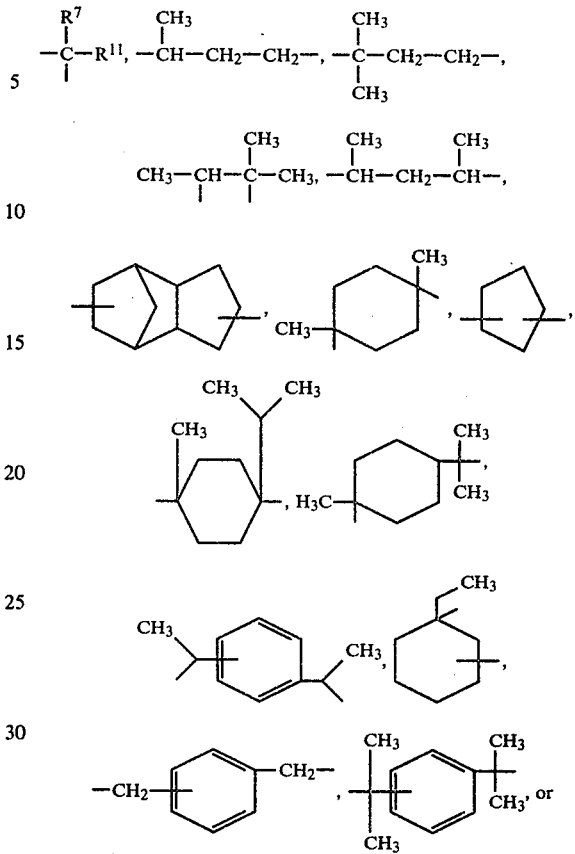

and, up to 60 mole percent, —S—, —CH$_2$—, —CH$_2$—S—CH$_2$— or —CH$_2$—O—CH$_2$—;

n represents an integer of from 1 to 29;

$R^6$ represents H, or a $C_1$–$C_{18}$-alkyl, a $C_5$–$C_{12}$-cycloalkyl, a $C_5$–$C_{12}$-cycloalkenyl, $C_7$–$C_{18}$-aralkyl which may optionally be substituted by OH—, SH—, ether, thioether, carbonic ester, carbonamide and carboxyl groups or which may be interrupted by such groups other than OH, SH and COOH— groups and olefinic double bonds,

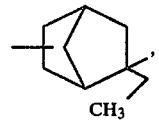

wherein $R^2$, $R^3$ and $R^4$ may be the same or different and represents H, a $C_1$–$C_{12}$-alkyl, a $C_5$–$C_{12}$-cycloalkyl, a $C_5$–$C_{12}$-cycloalkenyl, or a $C_7$–$C_{12}$-aralkyl, in addition to which, $R^2$ represents optionally-substituted aryl and, together with $R^4$ and the central C-atom, may form a 5- to 12-member aliphatic ring;

Z represents O, S, NH, $NR^5$, wherein $R^5=R^2$, or a radical of the formula CO—A—$R^2$, wherein A is a single bond, S, O, NH or $NR^2$, but where $R^2$ does not form a ring with $R^4$, or Z together with $R^3$ also represents

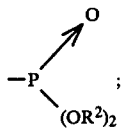

$R^7$ and $R^9$ may be the same or different and represent H, $CH_3$ or $C_2H_5$;

$R^8$ represents H, benzyl, styryl, α-methyl-styryl, tert.-butyl, tert.-amyl, isononyl, cyclohexyl, methyl cyclohexyl,

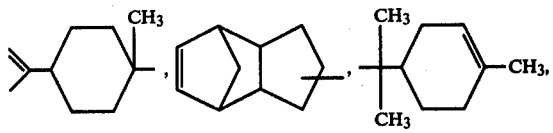

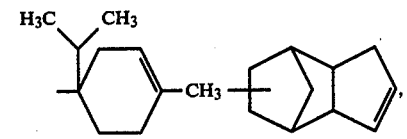

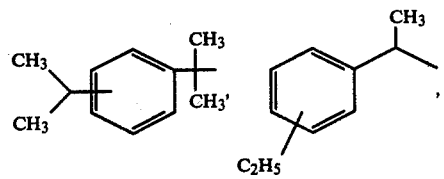

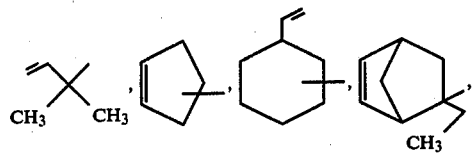

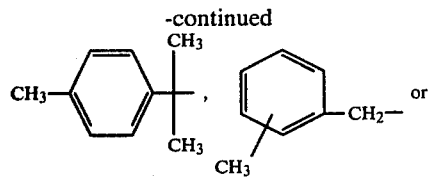

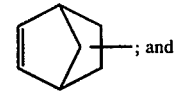

$R^{11}$ represents a $C_1$–$C_7$-alkyl, cyclohexyl, cyclohexenyl or aryl, characterized in that the aromatic amines corresponding to the formula:

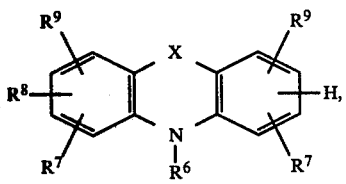

wherein $R^6$, $R^7$, $R^8$, $R^9$ and X are as defined above; are reacted with bifunctional compounds corresponding to the formulae Hal—Y—Hal, HO—Y—OH, $R^7$—Y—$OR^7$ or $R^7COO$—Y—$OCOR^7$, wherein Hal=halogen, and $R^7$ and Y are as defined above or with bis-olefins formed from these compounds by elimination of the radical HOH, $HOR^7$, HO-$COR^7$ or H—Hal, at temperatures in the range of from 50° to 300° C. in the presence of strong acids having $pk_s$-values of less than 2 and the radicals $R^9$ and $R^6$ (when not representing H) are introduced before, preferably during or after the above reaction of the amines.

6. A process according to claim 5, characterized in that $R^5$, $R^6$, $R^7$, $R^8$ and $R^9$ represent H; Y represents

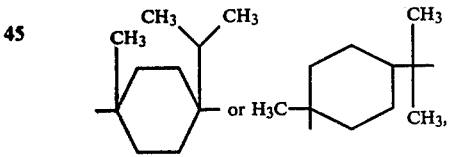

and that $R^9$ and $R^6$ are introduced after the above reaction of the amine.

* * * * *